United States Patent [19]

Moriuchi et al.

[11] Patent Number: 5,105,820
[45] Date of Patent: Apr. 21, 1992

[54] DISPOSABLE PRESSURE TRANSDUCER APPARATUS

[75] Inventors: Yousuke Moriuchi; Fumihisa Hirose, both of Fuji; Hazime Inacaki, Aichi; Atsusi Nakashima, Aichi; Isemi Igarashi, Aichi; Masashi Hashimoto, Aichi; Yasuhiro Goto, Aichi; Katsuhiro Minami, Aichi; Ritsuo Suzuki, Aichi, all of Japan

[73] Assignee: Terumo Kabushiki Kaisha, Tokyo, Japan

[21] Appl. No.: 605,252

[22] Filed: Oct. 29, 1990

Related U.S. Application Data

[62] Division of Ser. No. 409,015, Sep. 18, 1989.

[30] Foreign Application Priority Data

Sep. 22, 1988 [JP] Japan ................... 63-236485
Jul. 31, 1989 [JP] Japan ................... 1-196512

[51] Int. Cl.⁵ .................................................. A61B 5/02
[52] U.S. Cl. ................................. 128/675; 128/673; 128/748
[58] Field of Search ............. 128/672, 673, 675, 748

[56] References Cited

U.S. PATENT DOCUMENTS

| | | | |
|---|---|---|---|
| 4,431,009 | 2/1984 | Marino, Jr. et al. | 128/675 |
| 4,545,389 | 10/1985 | Schaberg et al. | 128/675 |
| 4,648,868 | 3/1987 | Hardwick et al. | 128/675 |
| 4,683,894 | 8/1987 | Kodama et al. | 128/675 |
| 4,819,653 | 4/1989 | Marks | 128/673 |
| 4,834,108 | 5/1989 | Vaillancourt | 128/673 |
| 4,947,856 | 8/1990 | Beard | 128/673 |
| 4,949,723 | 8/1990 | Wallace et al. | 128/675 |
| 4,970,900 | 11/1990 | Shepherd et al. | 128/675 |

Primary Examiner—Lee S. Cohen
Assistant Examiner—K. M. Pfaffle
Attorney, Agent, or Firm—Frishauf, Holtz, Goodman & Woodward

[57] ABSTRACT

A disposable pressure transducer for measuring fluid pressure, which includes a sensor assembly in a housing. The housing includes a fluid chamber and a sensor-accommodating chamber which are formed integrally with each other. The sensor assembly comprises: a sensor chip for converting pressure into an electrical signal; an insulating board on which the sensor chip is mounted and which is provided with an integrated-circuit for processisng an output signal of the sensor chip so that an external measuring device can read the signal; a cylindrical coupling lid which is bonded to the board in such a manner as to surround the sensor chip and which is fitted into a communication through-hole which provides communication between the fluid chamber and the sensor-accommodating chamber of the housing; a pressure-transmitting medium charged into the interior of the coupling lid so as to provide electrical insulation between the fluid chamber and the sensor chip; and an electrical cable connected to the board and electrically connected to the external measuring device.

10 Claims, 11 Drawing Sheets

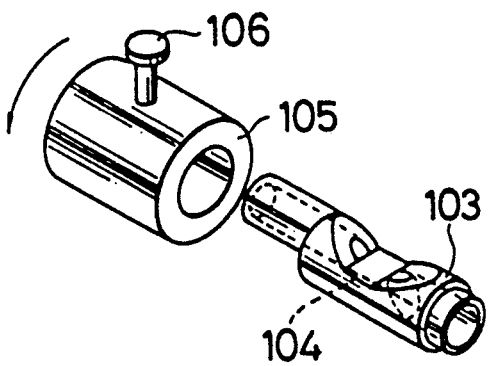
FIG.11 (A)
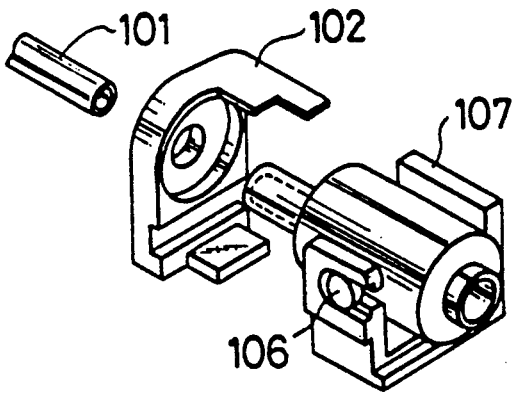
FIG.11(B)
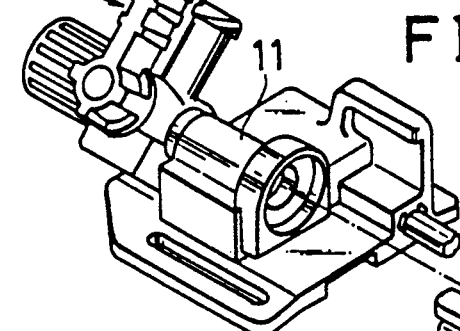
FIG.11(C)
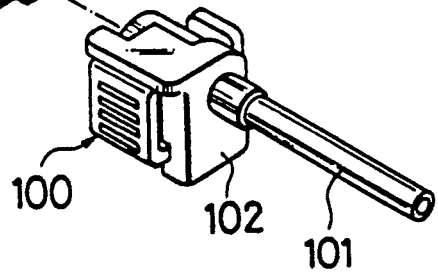
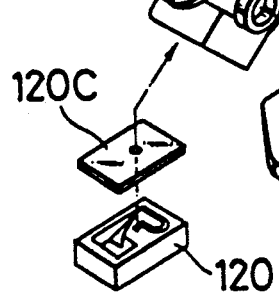
FIG.11(D)
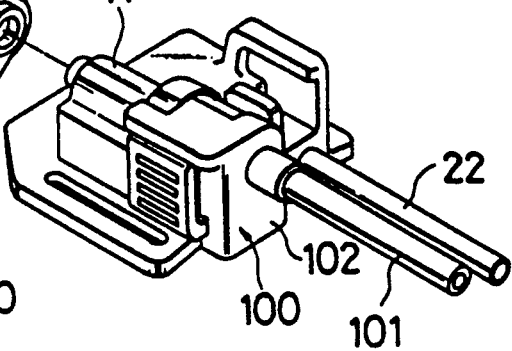

DISPOSABLE PRESSURE TRANSDUCER APPARATUS

This is a division of application Ser. No. 07/409,015 filed Sept. 18, 1989.

BACKGROUND OF THE INVENTION

1. Industrial Field

The present invention relates to a disposable pressure transducer and a disposable pressure transducer apparatus which are used in the field of medicine and, more particularly, to a disposable pressure transducer and a desposable pressure transducer apparatus which are used for measuring the blood pressure of an organism, the inner pressure of the uterus, the inner pressure of the bladder, the pressure in the cesophagus, or other particular pressure.

2. Prior Art

In order to cure a human or an animal or to diagnose the physiological state thereof, a particular kind of pressure such as the blood pressure of the organism is measured. For examle, in the case of measurement of the blood pressure of a human being, either an indirect measurement method or a direct measurement method is used to measure the blood pressure of a patient. In the former indirect measurement method which has heretofore been used, a pressure cuff and auscultation are utilized in combination, and a number of domestic sphygmomanometers have also recently been utilized. Such an indirect measurement method is advantageous in that neither pain nor burden is imposed on the patient, but it is disadvantageous in terms of the accuracy of measurement and continuity in monitoring. On the other hand, the direct measurement method is a method of measuring blood pressure by sticking an indwelling needle or a catheter into an artery of the arm of a patient and connecting an external pressure gauge by means of a liquid such as a Ringer solution. Although imposing pain on the patient, the direct measurement method has been more widely used than the indirect measurement method with respect to a patient who is being cured in an operating room or an intensive care unit. This is because since blood pressure can be measured at the same time as execution of blood operations such as sampling of blood and injection of remedy, high-precision measurement of the blood pressure is realized and long-time continuous monitoring is enabled.

Sphygmomanometers of the type utilized in the direct measurement method are called "external pressure transducer apparatus". The development of the external pressure transducer apparatus has a long history and they have been used in a wide range of applications. Such an external pressure transducer apparatus previously employed a metal-foil strain gauge as a pressure-electricity conversion element. However, with the remarkable advances in semiconductor technology, pressure transducer apparatus which utilize semiconductor strain gauges have been used in the medical field. Such a semiconductor strain gauge is formed by preparing single-crystal silicone as a material and effecting thermal diffusion of impurities or ion implantation on a surface of the single-crystal substrate. Because of the high elasticity inherent in the material, the semiconductor strain gauge is commonly formed in the shape of a beam or a diaphragm.

The problem of infection with hepatitis or an AIDS virus has recently arisen and the reuse of a pressure transducer in blood-pressure measurement has come into question. To cope with these problems, semiconductor technology which can yield devices of miniature size, high accuracy and mass-producibility has been noticed and development of disposable pressure transducer (disposable sphygmomanometers) has been vigorously conducted.

A conventional type of disposable pressure transducer is described in Japanese Patent Laid-Open No. 197730/1987. This pressure transducer includes a sensor assembly in its housing, and the sensor assembly is produced by ①bonding a sensor chip to a hermetically sealing disk, ② bonding the hermetically sealing disk to an intermediate housing, ③ fixing an integrated circuit board to the intermediate housing, ④ connecting the sensor chip to electrical connecting terminals on the board, ⑤ bonding a cylindrical coupling lid to the intermediate housing, and ⑥ charging a pressure-transmitting medium into the interior of the coupling lid.

Problems to be Solved by the Invention

In order to realize a disposable pressure transducer, it is necessary to assure a low price because of its disposability and yet excellent operability and measurement performance. In order to realize the low price, it is necessary to reduce the number of parts to be used and also to enhance the efficiency of the assembly operation.

However, the above-described conventional disposable pressure transducer has the following problems.

ⓐ Both the intermediate housing of the hermetically sealing disk which surrounds the sensor chip and the inner space of the coupling lid becomes complicated due to, for example, the projection of a board coupling piece provided with the electrical connecting terminals. As a result, stagnant air easily accumulates during the step ⑥ of charging the pressure-transmitting medium, and the pressure transmission characteristics may deteriorate.

ⓑ Although the sensor assembly in itself may constitute the central portion for pressure conversion, the sensor assembly includes a large number of constituent parts such as the sensor chip, the hermetically sealing disk, the intermediate housing, the integrated circuit board, the coupling lid and the like. This means that a large number of assembly steps are needed and that the aforesaid step ④ of electrically connecting (wire-bonding) the sensor chip and the board must be carried out in a narrow space within the intermediate housing; that is to say, the efficiency of the assembly operation is inferior.

ⓒ The flushing device, which serves to connect the pressure transducer to the external sterilized-liquid supply source, may be connected to the inlet side of the housing, or a three-way stop cock, which serves to alter the flow passage of a liquid, may be connected to the outlet side of the housing. In either case, however, the operation of connecting the flushing device or the three-way stop cock, hence a certain connection length, is needed. This means that the burden imposed on medical workers is increased and that the dynamic response of pressure sensing is made to fall, which hinders the accuracy of pressure measurement.

It is an object of the present invention to provide a disposable pressure transducer in which, although a sensor assembly in itself constitutes the central portion for pressure conversion, the construction of the sensor assembly is simple and pressure transmission characteristics are improved, and in which the number of constituent parts of the sensor assembly is small and the assembly process, hence the assembly operation, is simple, and which can be safely handled and is excellent in measurement performance.

It is another object of the present invention to provide a disposable pressure transducer apparatus of the type which is used with its pressure transducer connected to an external sterilized-liquid supply source or with its three-way stop cock for altering the flow passage of a liquid connected to the outlet side of a housing, which apparatus makes it possible to improve the accuracy of pressure measurement and to reduce the burden imposed on medical workers and which is safe and has excellent measurement performance.

DISCLOSURE OF THE INVENTION

To these ends, a disposable pressure transducer in accordance with the present invention defined in claim 1, includes a sensor assembly in a housing and which is used for measuring fluid pressure, characterized in that (A) the housing includes a fluid chamber provided with an inlet and an outlet and a sensor-accommodating chamber which communicates with the fluid chamber, the fluid chamber and the sensor-accommodating chamber being formed integrally with each other, and in that (B) the sensor assembly comprises a sensor chip for converting pressure into an electrical signal, an insulating board on which the sensor chip is mounted and which is provided with integrated-circuit means for processing an output signal of the sensor chip so that an external measuring device can read the signal, a cylindrical coupling lid which is bonded to the board in such a manner as to surround the sensor chip and which is fitted into a communication through-hole which provides communication between the fluid chamber and the sensor-accommodating chamber of the housing, a pressure-transmitting medium charged into the interior of the coupling lid so as to provide electrical insulation between the fluid chamber and the sensor chip, and an electrical cable connected to the board and electrically connected to the external measuring device.

Thus, a feature of the present invention defined in claim 2 is that an inner wall surface of the fluid chamber of the housing is treated with a hydrophilic treatment.

Another feature of the present invention defined in claim 3 is that at least a downstream portion of the fluid chamber as viewed in the direction in which a fluid flows in the housing has a flow passage area which progressively varies.

Another feature of the present invention defined in claim 4 is that the ratio of the area of a diaphragm portion on which a pressure sensitive gauge portion of the sensor chip is formed to the cross-sectional area of an inner space of the coupling lid which is charged with a pressure-transmitting medium is 5 or more.

Another feature of the present invention defined in claim 5 is that the inner diameter of a communicaiton through-hole which provides communication between the sensor-accommodating chamber and the fluid chamber of the housing is tapered so as to progressively diverge toward the sensor-accommodating chamber, the outer diameter of the coupling lid having a taper which corresponds to the aforesaid taper.

Another feature of the present invention defined in claim 6 is that the coupling lid is made from an injection molding, at least two projections being provided on the bottom of the coupling lid, and recesses being formed in the insulating board at positions corresponding to these projections. The coupling lid and the board can be positioned relative to each other by placing the projections and the corresponding recesses in alignment with each other.

Another feature of the present invention defined in claim 7 is that the housing and the coupling lid are made of the same material.

Another feature of the present invention defined in claim 8 is that the sensor chip is made from a semiconductor pressure sensor chip and is bonded to the board so that the top surface of the chip which is provided with the pressure sensitive gauge portion faces the fluid chamber, a small through-hole for communication with atmosphere is formed in the board at a location immediately below the chip.

Another feature of the present invention defined in claim 9 is further comprising with an adjusting circuit for adjusting the electrical characteristics of the semiconductor pressure sensor chip, a plurality of leads connected to the pressure sensor chip and the adjusting circuit, a plurality of flat teminal portions which are formed on the reverse surface of the board on which are mounted the pressure sensor chip and the adjusting circuit, the flat terminal portions being connected to the respective terminals of the pressure sensor chip and the adjusting circuit, a lid attached to the housing for accommodating this board so as to cover the reverse surface of the board, a plurality of contact pieces made of elastic material and disposed between this lid and aforesaid board in such a manner that, when the lid is attached to the housing, the contact pieces are pressed against the corresponding flat terminal portions, the contact pieces are connected to a lead which are connected to said measuring device.

Another feature of the present invention defined in claim 10 is that the sensor chip is bonded to the insulating board by soft adhesion.

Another feature of the present invention defined in claim 11 is that the pressure-transmitting medium is made of a silicone gel.

Another feature of the present invention defined in claim 12 is that the sensor chip, and the associated wiring which are surrounded on the insulating board by the coupling lid, and coated with a thin film of fluororesin.

Also, a disposable pressure transducer apparatus in accordance with the present invention defined in claim 13 comprises a pressure transducer capable of converging the fluid pressure into an electrical signal and provided with a flow passage for the liquid, a flow control device connected to the flow passage and which is capable of being connected to an external sterilized-liquid supply source and of restricting the flow rate of the liquid, and a three-way stop cock, the three-way stop cock comprising a valve box, and a valve rotatably disposed in the valve box, the valve box being provided with a first communication port connected to the flow passage, a second communication port connected to a path for transmitting the pressure of a fluid to be measured, the first and second communication ports being located in alignment with each other, and a third communication port located in the direction perpendicular to a straight line which connects the first and second communication ports, the valve being provided with three channels which perpendicularly intersect in a T-like configuration and being capable of placing the three communication ports in communication with one another, the pressure transducer, the flow control device and the three-way stop cock being integrally combined.

Also a disposable pressure transducer apparatus in accordance with the present invention defined in claim 14 comprises a pressure transducer capable of converting the fluid pressure into an electrical signal and provided with a flow passage for the liquid, a pressure-waveform correcting device which communicate with the flow passage and arranged to damp an anomalous pressure wave which is transmitted to the pressure transducer, and a three-way stop cock, the three-way stop cock comprising a valve box, and a valve rotatably disposed in the valve box, the valve box being provided with a first communication port connected to the flow passage, a second communication port connected to a path for transmitting the fluid pressure to be measured, the first and second communication ports being located in alignment with each other, and a third communication port located in the direction perpendicular to a straight line which connects the first and second communication ports, the valve being provided with three channels which perpendicularly intersect in a T-like configuration and being capable of placing the three communication ports in communication with one another, the pressure transducer, the pressure-waveform correcting device and the three-way stop cock being integrally combined.

Also, a disposable pressure transducer apparatus in accordance with the present invention defined in claim 15 is that the pressure-waveform correcting device is provided with an air chamber and a resistance portion which communicate with the flow passage and arranged to damp an anomalous pressure wave which is transmitted to the pressure transducer when the liquid in the flow passage flows into the air chamber through the resistance portion.

Also, a disposable pressure transducer apparatus in accordance with the present invention defined in claim 16 comprises a pressure transducer capable of converting the fluid pressure into an electrical signal and provided with a flow passage for the liquid, a flow control device capable of being connected to an external sterilized-liquid supply source and of restricting the flow rate of the liquid, a pressure-waveform correcting device which communicate with the flow passage and arranged to damp an anomalous pressure wave which is transmitted to the pressure transducer, and a three way stop cock, the three way stop cock comprising a valve box, and a valve rotatably disposed in the valve box, the valve box being provided with a first communication port connected to the flow passage, a second communication port connected to a path for transmitting the pressure of a fluid to be measured, the first and second communication ports being located in alignment with each other, a third communication port located in the direction perpendicular to a straight line which connects the first and second communication ports, and a fourth communication port which opposes the third communication port, the valve being provided with three channels which perpendicularly intersect in a T-like configuration and the pressure transducer, the flow control device, the pressure-waveform correcting device and the three-way stop cock being integrally combined.

Also, a disposable pressure transducer apparatus in accordance with the present invention defined in claim 17 is that the pressure-waveform correcting device is provided with an air chamber and a resistance portion which communicate with the flow passage and arranged to damp an anomalous pressure wave which is transmitted to the pressure transducer when the liquid in the flow passage flows into the air chamber through the resistance portion.

Also, a disposable pressure transducer apparatus in accordance with the present invention defined in claim 18 is that the three-way stop cock is capable of placing at least three of the first to fourth communication ports in communication with one another.

Another feature of the present invention defined in claim 19 is that an inner wall surface of the fluid chamber of the housing is treated with a hydrophilic treatment, at least a downstream portion of the fluid chamber as viewed in the direction in which a fluid flows in the housing having a flow passage area which varies progressively, the ratio of the area of a diaphragm portion on which a pressure sensitive gauge portion of the sensor chip is formed to the cross-sectional area of an inner space of the coupling lid which is charged with a pressure-transmitting medium being 5 or more, the distance between the pressure transducer and the flow control device being selected to be equal to or less than 3% of the overall length of the path for transmitting the fluid pressure to be measured, which path starts at the pressure transducer, and the resistance portion of the pressure-waveform correcting device being formed in a plane in a serpentine manner.

Another feature of the present invention defined in claim 20 is that the aforesaid three-way stop cock comprises a valve box and a valve rotatably disposed in the valve box. The valve box is provided with a first communication port connected to the flow passage and a second communication port connected to a path for transmitting the fluid pressure to be measured, the first and second communication ports being located in alignment with each other, and a third communication port located in the direction perpendicular to a straight line which connects the first and second communication ports. The valve is provided with three channels which perpendicularly intersect in T-like configuration and is capable of placing at least two of the three communication ports in communication with each another.

Another feature of the present invention defined in claim 21 is that the valve box of the aforesaid three-way stop cock further includes a fourth communication port which opposes the third communication port, the valve being provided with three channels which perpendicularly intersect in a T-like configuration and being capable of placing at least three of the first to fourth communication port in communication with one another.

Another feature of the present invention defined in claim 22 is that the resistance portion of the pressure-waveform correcting device is made from a straight line, a curve, a combination of straight and curved lines, or a combination of different straight lines, the air chamber being connected to the terminal end of the fluid passage.

The invention described in claim 1 includes a sensor assembly in a housing, and the sensor assembly is produced by ① directly bonding a sensor chip to an insulating board provided with an integrated circuit, ② bonding the sensor chip to the electrical connecting terminals of the board, ③ bonding a cylindrical coupling lid to the board, and ④ charging a pressure-transmitting medium into the interior of the coupling lid. Accordingly, the following advantages (1a) and (1b) are obtained.

(1a) The inner space of the coupling lid which surrounds the sensor chip on the board is formed as a simple space with no projection therein. Accordingly, no stagnant air accumulates in the coupling lid during the above step (4) of charging the pressure-transmitting medium, and pressure transmission characteristics can be therefore improved. In addition, safety is ensured in that no air penetrates into a blood vessel.

(1b) Although the sensor assembly in itself constitutes the central portion for pressure conversion, it can be constructed from a small number of parts such as the sensor chip, the board, the coupling lid and the like. This advantage allows the number of assembly steps to be reduced and enables the above step (2) of electrically connecting the sensor chip and the board (wire bonding) to be conducted in a wide open space on the board. As a result, the efficiency of assembly operation improves.

The above (1a) and (1b) means that it is possible to provide a disposable pressure transducer in which the pressure transmission characteristics are improved, which makes it possible to reduce the number of assembly steps, thereby improving the efficiency of assembly operation, and which can be safely handled and excels in measurement performance.

In accordance with the present invention described in claim 2, the following advantage (2) is obtained.

(2) Since the inner wall surface of the fluid chamber of the housing has hydrophilic properties, air is prevented from remaining on this inner wall surface, whereby no stagnant air accumulates and the pressure transmission characteristics can therefore be improved. Moreover, safety is ensured in that no air penetrates into the blood vessel.

In accordance with the present invention described in claim 3, the following advantage (3) is obtained.

(3) While a flushing liquid such as a saline solution is being supplied in the direction of fluid flow in the fluid chamber of the housing, that is, while the flushing liquid is being supplied from the side of the fluid chamber which has a larger flow passage area, the flow velocity of the flushing liquid becomes gradually larger according as the cross-sectional area of the fluid passage becomes smaller. Accordingly, no stagnent air remains in the fluid passage. Since no stagenant air remains there, the pressure transmission characterisitics can be improved, and also safety is ensured in that no air penetrates into the blood vessel.

In accordance with the present invention described in claim 4, the following advantage (4) is obtained.

(4) It is possible to ignore pressure loss which results from shearing deformation which may occur when the pressure-transmitting medium made of a silicone gel comes into the inner-diameter portion of the coupling lid. Accordingly, stable and high-precision pressure measurement can be realized.

In this case, if the aforesaid ration is 5 or less, shearing forces will act on the peripheral portion of the pressure-transmitting medium and the fluid pressure to be measured is absorbed. As a result, the accuracy of measurement deteriorates.

In the present invention described in claim 5, the following advantage (5) is obtained.

(5) This coupling lid can be readily fitted into and fixed to the communication through-hole owing to the taper-coupling, and the fluid charged into the fluid chamber can be reliably maintained in a liquid-tight state.

In the present invention described in claim 6, the following advantage (6) is obtained.

(6) The engagement between the projections and the recesses serves as a guide when the coupling lid is to be bonded to the board. Accordingly, it is possible to easily achieve high-quality adhesion.

In the present invention described in claim 7, the following advantage (7) is obtained.

(7) Since the housing and the coupling lid are made of the same material (for example polycarbonate resin), the thermal expansion coefficients of both are the same with respect to factors such as variations in ambient temperature and the adhesion can therefore be kept strong. Adhesion using a solvent can also be used.

In the present invention described in claim 3, the following advantage (8) is obtained.

(8) Since the semiconductor pressure sensor chip is compact and highly sensitive, it is possible to realize high-precision pressure measurement even with a compact apparatus. A large number of uniform chips can be produced by mass-production technology for semiconductors, and such sensor chips are therefore suitable for use as disposable sensor chips. Moreover, since the pressure sensitive guage surface of the sensor chip on the board is disposed to face the fluid chamber, a substantial portion of fluid pressure is applied to the board so that this fluid pressure can be stably supported on the board. Further, since the small through-hole for communication with atmosphere is formed in the board at a location immediately below the chip, it is possible to realize stable pressure measurement based on atmospheric pressure.

In the present invention described in claim 9, the following advantage (9) is obtained.

(9) Since the semiconductor pressure sensor chip and the adjusting circuit are integrally provided on a common board, noise does not easily penetrate into any line that extends between these elements. Accordingly, resistance to noise is improved and the accuracy of measurement can therfore be improved. The connections between the leads and the semiconductor pressure sensor chip and the adjusting circuit are achieved by the abutment between the contact pieces and the flat terminal portions. Accordingly, it is possible to reduce the number of soldered portions compared to the prior art, and the above connetions can be achieved merely by attaching the lid to the housing. It is possible to prevent the pressure sensor chip and the adjusting circuit from being contaminated by flux components derived from the solder, and an improvement in the efficiency of assembly operation can be realized. In this structure, connections are only needed between the contact pieces and the flat terminal portions as well as between the contact pieces and the leads. Accordingly, the number of connections can be reduced compared to the prior art, and the reliability of connections therefore improves.

In the present invention described in claim 10, the following advantage (10) is obtained.

(10) Since the sensor chip is bonded to the insulating board by soft adhesion in the above-described state (9), the sensor chip does not undergo the influence of stress or thermal stress from the board, whereby stable and high-precision pressure measurement can be realized.

In the present invention described in claim 11, the following advantage (11) is obtained.

(11) Pressure fluctuations in the fluid chamber are transmitted to the sensor chip through the pressure-transmitting medium made of a silicone gel. Accordingly, it is possible to prevent the fluid from coming into contact with the sensor chip, whereby the sensor chip can stably sense the pressure fluctuations only.

In the present invention described in claim 12, the following advantage (12) is obtained.

(12) An organic coating employing fluororesin is applied to the entire sensor chip and is isolated from corrosion and unwanted electrical conduction due to the fluid. Accordingly, electrical safety with respect to the organism is ensured and, even if the apparatus is used for a long time, electrical safety with respect to the patient is not impaired.

In the present invention described in claim 13, the following advantage (13) is obtained.

(13) The inlet portion of the fluid chamber of the housing is integrally combined with a flow control device (flushing device) which can be connected to an external sterilized-liquid supply source and which is capable of limiting the flow rate of the sterilized liquid. The three-way stop cock, which can alter the flow passage of the liquid, is also provided integrally with the outlet portion of the fluid chamber. Accordingly, the operation of connecting the flow control device and the three-way stop cock is not needed and the burden imposed on medical workers can be lightened. Moreover, it is possible to minimize the flow-passage length required to incorporate the flow control device and the three-way stop cock, with the result that the dynamic response of pressure sensing is improved and the accuracy of pressure measurement can therefore be improved. (The frequency response of the fluid passage is determined by the material and the diameter of the fluid passage and the diameter of a sticking needle. Even if the length of the flow passage is slightly short, the resonance frequency rises and can therefore be separated from the frequency band contained in a pressure waveform, whereby high-precision measurement is enabled.)

There is no risk of any connected pipe being coming off since the pressure transducer, the flow control device and the three-way stop cock are integrally combined. This means that, even if the fluid to be measured is, for example, artery blood having a high pressure of 120–150 mmHg, safe operation is ensured in that there is no risk that the blood may spill due to accidental separation between the connections.

In accordance with the present invention described in claim 14 or 15, the following advantage (14) is obtained.

(14) It is essentially impossible to avoid the occurrence of resonance in a fluid circuit or the penetration of incidental bubbles. Accordingly, the pressure-waveform correcting device is aimed at improving dynamic response during pressure measurement, and is used in combination with the sensor transducer. As the position of the pressure-waveform correcting device which serves to eliminate resonance or the like is made closer to that of a pressure sensor, it is possible to more reliably eliminate the resonance which may occur between the pressure sensor and the pressure-waveform correcting device.

By switching the three-way stop cock, the path for transmitting the pressure of a fluid to be measured can be selectively connected to or shut off from the pressure tranducer, or the third communication port can be connected to the pressure-waveform correcting device (damping device). In addition, the damping device can be selectively connected to or shut off from the fluid passage, thereby enabling the effect of waveform correction to be observed. When the damping device is in no use, the damping device is shut off from the fluid flow passage to prevent the air in the air chamber from being expanded due to a temperature change and discharged from the air chamber. Accordingly, it is possible to keep constant the air capacity in the air chamber so that the damping performance can be maintained in a proper state.

In accordance with the present invention described in claim 16, 17 or 18, the following advantage (15) is obtained.

(15) The above advantages (13) and (14) are obtained at the same time.

In accordance with the present invention described in claim 19, the following advantage (16) is obtained.

(16) In addition to the above advantage (15), the following advantages ① to ⑤ are obtained.

① As a result of hydrophilic treatment, the aforesaid advantage (2) is obtained.

② Since the flow passage area is progressively varied, the aforesaid advantage (3) is obtained.

③ Since the area ratio is set to 5 or more, the aforesaid advantage (4) is obtained.

④ Since the distance between the pressure transducer and the flow control device be made equal to or less than 3% of the overall length of the path for transmitting the pressure of a fluid to be measured, which path starts at the pressure transducer, it is possible to ignore the influence which is exerted over the measurement accuracy of the pressure transducer by the resonance occurring between the pressure transducer and the flow control device. In this manner, the measurement performance can be improved.

⑤ The resistance portion of the pressure-waveform correcting device is made serpentine in a plane. Accordingly, even in a small space, it is possible to assure a long resistance component, hence the desired pressure damping performance, whereby improved measurement performance can be achieved even with a small apparatus.

In accordance with the present invention described in claim 20, the following advantage (17) is obtained.

(17) By switching the three-way stop cock, the path for transmitting the pressure of a fluid to be measured can be selectively connected to or shut off from the sensor chip, or the third communication port can be used for correction of pressure waveforms (damper), monitoring of pressure, injection of remedy, or sampling of blood.

In accordance with the present invention described in claim 21, the following advantage (18) is obtained.

(18) By switching the three-way stop cock, the path for transmitting the pressure of a fluid to be measured can be selectively connected to or shut off from the sensor assembly, or the third and fourth communication ports can be used for correction of pressure waveforms (damper), monitoring of pressure, injection of remedy, or sampling of blood.

In accordance with the present invention described in claim 22, the following advantage (19) is obtained.

(19) Since the resistance portion of the pressure-waveform correcting device is formed as a serpentine flow passage, it is possible to assure a relatively long fluid resistance component in an area of even the same size, whereby the desired pressure damping performance can be obtained.

BRIEF DESCRIPTION OF DRAWING

FIG. 11 is a diagrammatic view showing the sequence of the steps of assembling the pressure transducer apparatus;

BEST MODE FOR CARRYING OUT THE INVENTION

Figure 1:
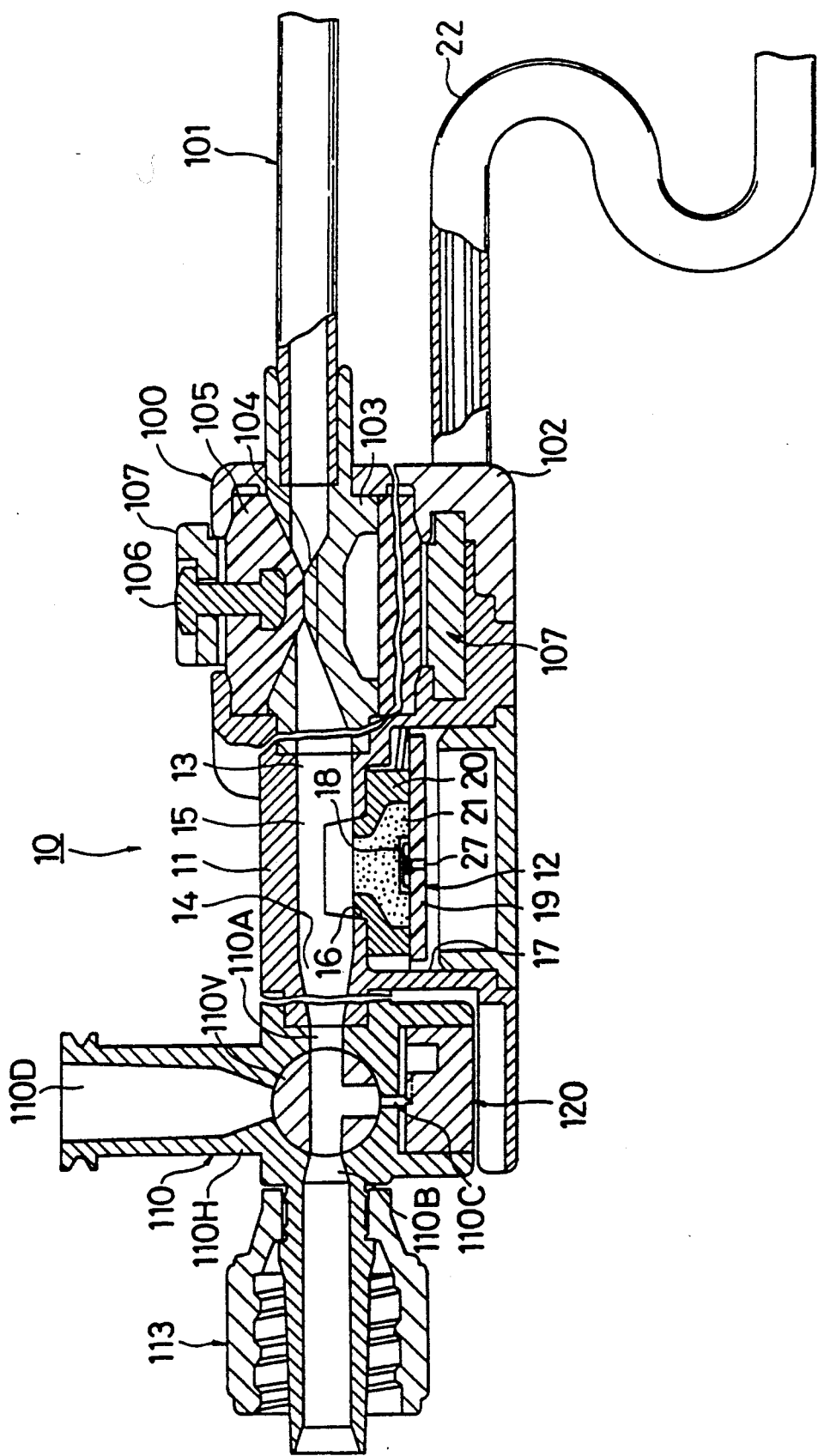
FIG. 1 is a cross-sectional view showing one example of a disposable pressure transducer apparatus according to the present invention.
Figure 2:
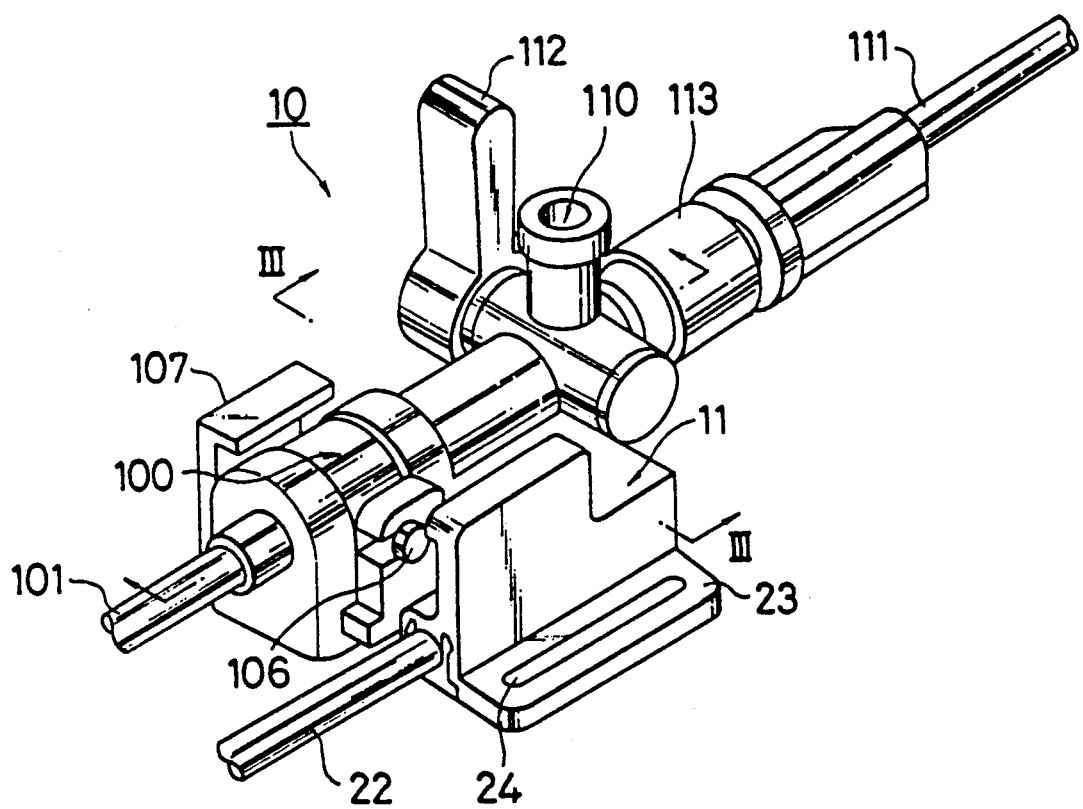
FIG. 2 is a perspective view showing the external appearance of the apparatus of FIG. 1.
Figure 3:
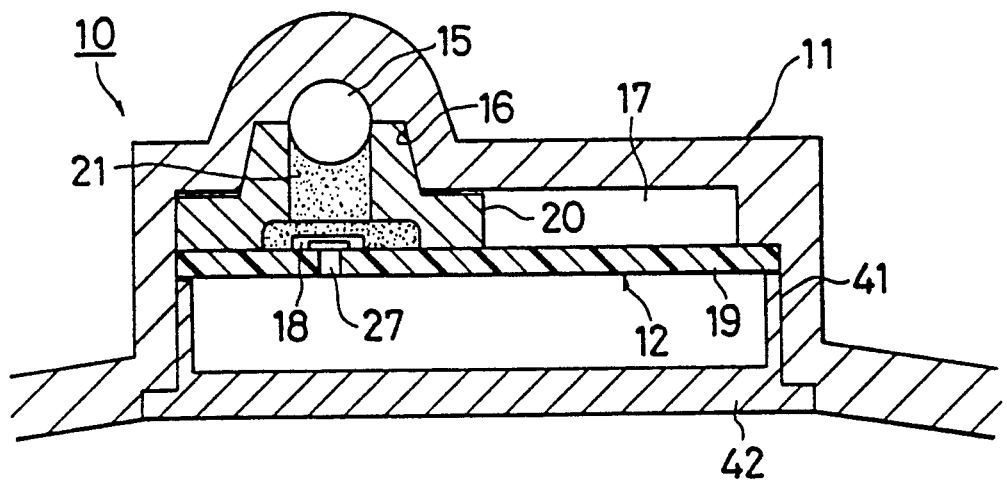
FIG. 3 is a cross-sectional view taken along line III—III of FIG. 2.

As shown in FIGS. 1, 2, 3 and 9, a disposable pressure transducer 10 has a sensor assembly 12 incorporated in a housing 11 and is arranged to measure fluid pressure.

The housing 11 is formed of a transparent plastic such as polycarbonate resin, and has a fluid chamber 15 and a sensor-accommodating chamber 17 which is formed integrally with the fluid chamber 15. The fluid chamber 15 is provided with an inlet 13 and an outlet 14, and the sensor-accommodating chamber 17 communicates with the fluid chamber 15 through a communication through-hole 15.

Figure 4:
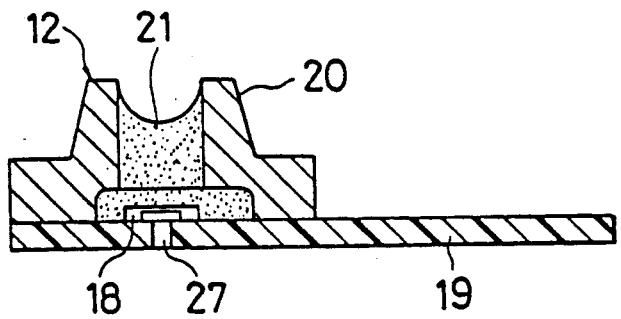
FIG. 4 is a cross-sectional view showing a sensor assembly.
Figure 5:
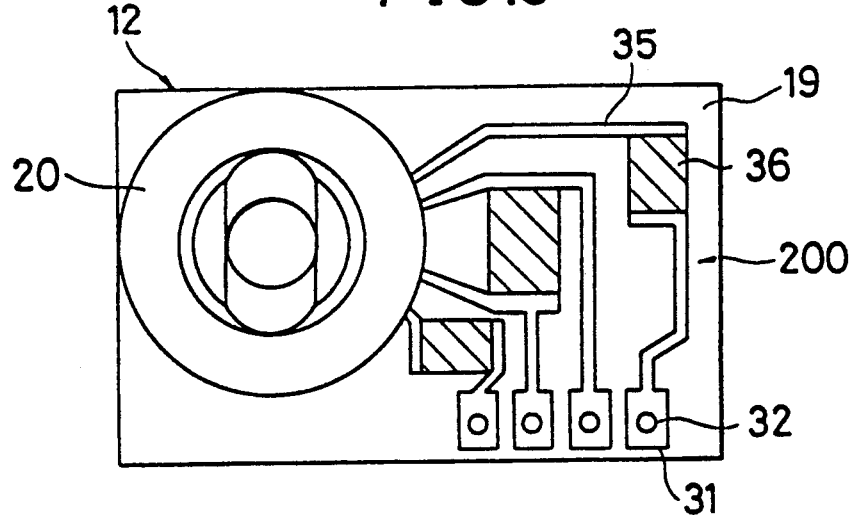
FIG. 5 is a plan view of the sensor assembly of FIG. 4.
Figure 6:
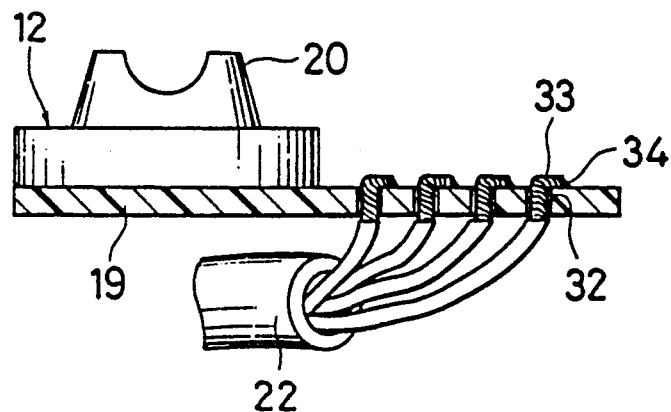
FIG. 6 is a diagrammatic view showing the connection structure between a board and an electrical cable.

As shown in FIGS. 4, 5 and 6, the sensor assembly 12 is constructed from a sensor chip 18, an insulating board 19, a coupling lid 20, a pressure-transmitting medium 21, and an electrical cable 22.

The sensor chip 18 converts pressure into an electrical signal. The insulating board 19, to which the sensor chip 18 is bonded, is provided with an integrated circuit means which serves to process the output signal of the sensor chip 18 so that that signal can be read into an external measuring device. The coupling lid 20 is of an cylindrical configuration, and is bonded to the board 19 to surround the sensor chip 18. The coupling lid 20 is securely fitted into the communication through-hole 16 which provides communication between the sensor-accommodating chamber 17 and the fluid chamber 15 within the housing 11. The pressure-transmitting medium 21 is charged into the inner space of the coupling lid 20 and serves as an electrical insulator between the fluid chamber 15 and the sensor chip 18. The electrical cable 22 is connected to the board 19, and is electrically connected to the external measuring device.

The above-described disposable pressure transducer 10 has the sensor assembly 12 incorporated in the interior of the housing 11. The sensor assembly 12 is assembled by ① directly bonding the sensor chip 18 to the insulating board 19, ② connecting the sensor chip 18 to electrical connection terminals of the board 19, ③ bonding the cylindrical coupling lid 20 to the board 19, and ④ charging the pressure-transmitting medium 21 into the interior of the coupling lid 20.

In operation, pressure fluctuations which have been transmitted from an organism to the fluid chamber 15 are transmitted to a diaphragm of the sensor chip 18 through the pressure-transmitting medium 21. The diaphragm of the sensor chip 18 is deflected by this pressure to cause a change in the resistance of a pressure sensitive gauge portion, which is formed on the surface of the diaphragm by thermal diffusion treatment. The electrical signal thus generated passes through wiring 35 and relay terminals 31, which are printed on the insulating board 19, and is in turn transferred over the electrical cable 22 to an external display or a recording device. Accordingly, the following advantages ① and ② are obtained.

① Although the sensor assembly 12 in itself constitutes the central portion for pressure conversion, it can be constructed from a small number of parts such as the sensor chip 18, the insulating board 19, the coupling lid 20 and the like. This advantage allows the number of assembly steps to be reduced and enables the above step ② of electrically connecting the sensor chip 18 and the board 19 (wire bonding) to be conducted in a wide open space on the board 19. As a result, the efficiency of assembly operation improves.

② The inner space of the coupling lid 20 which surrounds the sensor chip 18 on the board 19 is formed as a simple space with no projection therein. Accordingly, no stagnant air accummulates during the above step ④ of charging the pressure-transmitting medium 21 and pressure transmission characteristics can be therefore improved.

In addition, the inner wall surface of the fluid chamber 15 of the housing 11 has hydrophilic properties imparted by plasma treatment. Accordingly, the following advantage ⓐ is obtained.

ⓐ Since the inner wall surface of the fluid chamber 15 of the housing 11 has hydrophilic properties, air is prevented from remaining on this inner wall surface, whereby no stagnant air accumulates and the pressure transmission characteristics can therefore be improved. Moreover, safety is ensured in that no air enters the organism.

The flow passage area of a downstream portion of the fluid chamber 15 as viewed in the direction in which a fluid flows in the housing 11 from the inlet 13 to the outlet 14, that is to say, the flow passage area of the portion of the fluid chamber 15 which is near the outlet 14 has a flow passage area which progressively varies in such a manner that the diameter of that portion becomes gradually smaller toward the outlet 14. Accordingly, the following advantage ⓑ is obtained.

(b) While a flushing liquid such as a saline solution or the like is being supplied from the side on which the flow passage area is larger as viewed in the direction in which the liquid advances through the fluid chamber 15 of the housing 11, the flow velocity of the flushing liquid becomes gradually larger according as the flow passage area of the flow passage becomes smaller. Accordingly, no stagnant air remains in the flow passage. Since no stagnant air remains, the pressure transmission characteristics can be improved, and safely can be ensured in that no air penetrates into the blood vessel.

The communication through-hole 16 which provides communication between the sensor-accommodating chamber 17 and the fluid chamber 15 in the housing 11 is tapered in such a manner that the inner diameter of the through-hole 16 becomes progressively larger toward the sensor-accommodating chamber 17. The coupling lid 20 also has a tapered outer periphery which corresponds to the aforesaid taper. The coupling lid 20 has a stepped portion below its taper. The coupling lid 20, whose tapered outer periphery is fitted into the tapered inner periphery of the communication through-hole 16, is fixed to the housing 11 by an adhesive. This adhesive is applied to both the stepped portion of the coupling lid 20 which is formed below its taper and a peripheral portion of the lower edge of the taper of the communication through-hole 16 of the housing 11.

Accordingly, the above-described pressure transducer 10 provides the following advantage (c).

(c) The coupling lid 20 can be readily fitted into and fixed to the communication through-hole 16 of the housing 11 owing to the taper coupling, and the fluid charged into the fluid chamber 15 can be reliably maintained in a liquid-tight state. The fluid charged into the fluid chamber 15 is sealed by the aforesaid taper coupling of the communication through-hole 16 and the coupling lid 20 and, in addition, is sealed by the adhesion between the aforesaid stepped portion of the coupling lid 20 and the inner surface of the housing 11. As a result, it is possible to reliably prevent the fluid from leaking from the fluid chamber 15.

Figure 7:
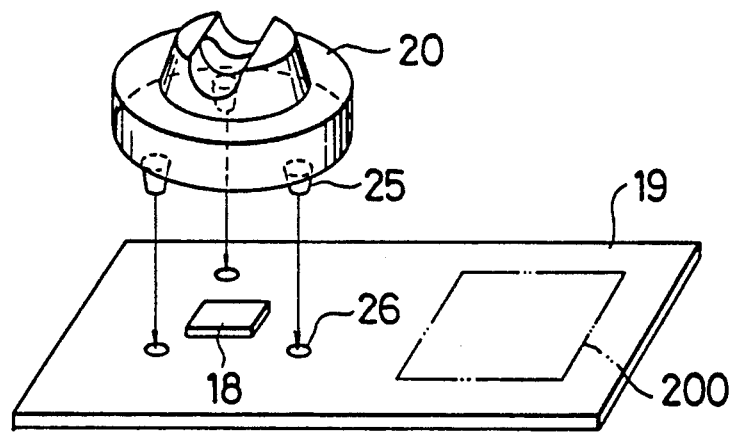
FIG. 7 is a perspective view showing the bonding structure between the board and a coupling lid.

The coupling lid 20 is made from an injection molding and, as shown in FIG. 7, three projections 25 are provided on the bottom of the coupling lid 20. Recesses 26 are formed in the insulating board 19 at positions corresponding to the projectins 25. The coupling lid 20 and the board 19 are positioned relative to each other by placing the projections 25 and the corresponding recesses 26 in alignment with each other.

Accordingly, the aforesaid pressure transducer 10 provides the following advantage (d).

(d) The engagement between the projections 25 and the recesses 26 serves as a guide when the coupling lid 20 is to be bonded to the board 19. Accordingly, it is possible to easily achieve high-quality adhesion.

Incidentally, it is not always necessary to form the projections 25 and the recesses 26.

The housing 11 and the coupling lid 20 are made of the same material.

Accordingly, the aforesaid pressure transducer 10 provides the following advantage (e).

(e) Since the housing 11 and the coupling lid 20 are made of the same material, the thermal expansion coefficients of both are the same with respect to factors such as variations in ambient temperature. Accordingly, the adhesion can be kept strong. Adhesion using a solvent can also be used.

More specifically, the sensor assembly 12 is formed primarily of polycarbonate resin so that it is possible to suppress thermal stress or strain resulting from a combination of composite materials. Accordingly, little strain occurs in the sensor assembly 12 during assembly thereof, and little thermal strain is generated due to temperature changes during use, whereby the characteristics of the sensor assembly 12 can be kept stable for a long time. In addition, since the required performance can be assured with a single sensor assembly alone, it is possible to realize a reduction in the number of assembly steps, hence a reduction in cost.

The sensor chip 18 is made from a semiconductor pressure sensor chip which utilizes the piezoresistance effect of a silicone semiconductor. A silicone diaphragm is formed by effecting chemical etching of the middle portion of the reverse side of a thin rectangular silicone board, and a pressure sensitive gauge portion is integrally formed on each of the middle portion and the edge portions of the surface of the silicone diaphragm. In this manner, a bridge circuit is formed. This silicone diaphragm, which has a high degree of springiness and high elasticity, is suitable for use as a pressure transducer. In addition, the sensor chip 18 is bonded to the board 19 so that the top surface of the chip 18 which is provided with the pressure sensitive gauge portion faces the fluid chamber 15, and a small through-hole 27 for communication with atmosphere is formed in the board 19 at a location immediately below the chip 18. The board 19 is formed of a ceramic material such as alumina.

Accordingly, the above-described pressure transducer 10 provides the following advantage (f).

(f) Since the semiconductor pressure sensor chip 18 is compact and highly sensitive, it is possible to realize high-precision pressure measurement even with a compact apparatus. A large number of uniform chips 18 can be produced by mass-production technology for semiconductors, and the sensor chips 18 are therefore suitable for use as disposable sensor chips. Moreover, since the pressure sensitive gauge surface of the sensor chip 18 on the board 19 is disposed to face the fluid chamber 15, a substantial portion of fluid pressure is applied to the board 19 so that this fluid pressure can be stably supported on the board 19. Further, since the small through-hole 27 for communication with atmosphere is formed in the board 19 at a location immediately below the chip 18, it is possible to realize stable pressure measurement based on atmospheric pressure.

In addition, the aforesaid semiconductor pressure sensor chip 18 has a compact size and high performance, and strain gauges and formed on the four sides of the diaphragm surface having a small area so as to compensate for the instability of the output due to temperature changes. Since deformation in the diaphragm is small, the dynamic response is good, whereby high-precision pressure measurement can be realized.

The electrical cable 22 includes a plurality of conductors 33. These conductors 33 are inserted into terminal holes 32 formed in the respective relay terminals 31 of the insulating board 19 and are exposed at the relay terminals 31 by soldering at 34. The electrical cable 22 has a hollow structure in order to allow for communication with atmosphere (refer to FIG. 6).

Printed on the surface of the insulating board 19 are, in addition to the wiring 35 for forming the bridge circuit, an adjusting resistor for matching the bridge resistance to the impedance of an external measuring device and an adjusting circuit 200 including an adjusting resistor 36 for adjusting the pressure sensitivity. The adjusting circuit 200 serves to adjust the electrical characteristics of the pressure sensor chip 18, such as offset voltage, sensitivity and the like. Although not shown in detail, the adjusting circuit 200 includes a thick-film resistor or the like for forming the bridge circuit, and the aforesaid adjustment is made by adjusting the resistance value of the thick-film resistor by, for example, laser trimming.

Figure 15:
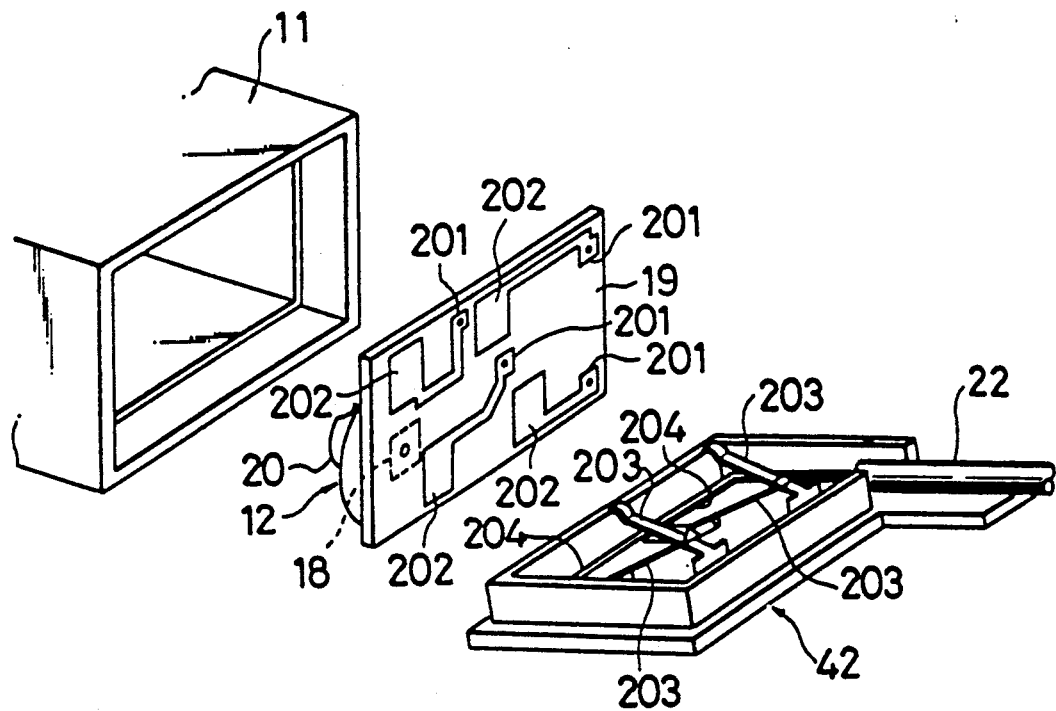
FIG. 15 is a perspective view showing in exploded form the connection structure between the board and the electrical cable.
Figure 16:
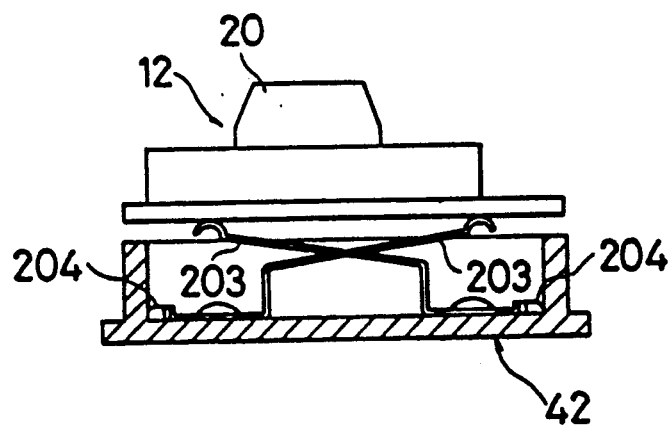
FIG. 16 is a cross-sectional view showing in assembled form the connection structure between the board and the electrical cable.

In the above-described pressure transducer 10, the connection between the electrical cable 22 and the sensor chip 18 and the adjusting circuit 200 on the board 19 may be implemented as shown in FIGS. 15, and 16. More specifically, as shown in FIG. 15, four terminals 201 (which are terminals for connection with an electrical power source and for detection-signal output) are formed on the reverse surface of the board 19, the four terminals 201 being conducted through through-holes from the pressure sensor chip 18 and the adjusting circuit 200. Four flat terminal portions 202 are also formed on the reverse surface of the board 19 in such a manner that they are spaced apart at predetermined intervals. These flat terminal portions 202 are connected to the respective terminals 201 through wiring patterns. An Au thin film for reducing contact resistance is formed on the surface of each of the flat terminal portions 202. The board 19 is accommodated in the interior of the housing 11 through a rectangular opening thereof with the top surface of the board 19 (the surface of the board 19 on which the sensor chip 18 is disposed) facing the interior of the housing 11. A reverse lid 42 is attached to the housing 11 so as to cover the reverse surface of the board 19. Four contact strips 203, made of conductive elastic material (phosphor bronze, beryllium copper or the like), are disposed on the reverse lid 42 so as to extend in the obliquely upward directions. Although not shown, the proximal end of each of the contact strips 203 is fixed to the reverse lid 42 by fitting, for example, a hole formed in the proximal end portion onto a projection integral with the reverse lid 42 collapsing the projection by fusion. The contact strips 203 are configured such that, when the reverse lid 42 is attached to the housing 11, the free ends of the respective contact strips 203 are pressed against the corresponding flat terminal portions 202 formed on the reverse surface of the board 19. An Au thin film for reducing contact resistance is formed on the surface of each of the contact strips 203. One end of each of four leads 204 for supplying electrical power to the board 19 and for extracting signals therefrom is connected, as by pinching, to the proximal end of each of the contact strips 203. These leads 204 are extended out of the apparatus in the form of the electrical cable 22.

With the above-described structure shown in FIGS. 15 and 16, the following advantage (g) is obtained.

(g) The connections between the leads 204 and the pressure sensor chip 18 and the adjusting circuit 200 are achieved by the abutment between the contact strips 203 and the flat terminal portions 202, and the connections between the leads 204 and the contact strips 203 are formed by pinching. Accordingly, it is possible to reduce the number of soldered portions compared to the prior art, whereby it is possible to prevent the board 19 from being contaminated by flux components derived from the solder. The contact strips 203 can be connected to the respective flat terminal portions 202 merely by attaching the reverse lid 42 to the housing 11. This feature enables an improvement in the efficiency of the assembly operation in combination with a reduction in the number of soldered portions. In this structure, connections are only needed between the contact strips 203 and the flat terminal portions 202 as well as between the contact strips 203 and the leads 204. Accordingly the number of connections can be reduced compared to the prior art, and the reliability of connections improves.

Accordingly, with the above-described pressure transducer 10, the characteristics can be stabilized, since the sensor chip 18 is mounted on the board 19 and the thick-film resistor on the board 19 is trimmed after a gel has been charged. The required constituent parts are mounted in advance on a single board 19 and the sensor assembly 12 can therefore be handled as one component. Accordingly, since compensation for the performance can be implemented with the board 19 alone, good handling can be achieved. Since the sensor chip 18 and the adjusting circuit 200 are provided on the identical board 19, excellent temperature characteristics are obtained.

The sensor chip 18 is softly bonded to the insulating board 19 by silicone resin.

Accordingly, the aforesaid pressure transducer 10 provides the following advantage (h).

(h) Since the sensor chip 18 is softly bonded to the insulating board 19, the sensor chip does not undergo the influence of stress or thermal stress from the board 19 or environments, whereby stable and high-precision pressure measurement can be realized. As described previously, pressure, which is applied to the upper surface of the diaphragm of the sensor chip 18, hence the sensor chip 18 itself, is substantially supported by the insulating board 19. Accordingly, the aforesaid soft bonding has no effect on the supporting ability of the board 19 with respect to the sensor chip 18.

In general, fixing or soft bonding is available as the method of mounting a semiconductor pressure sensor chip on a board. The fixing is the process of integrally bonding the sensor chip to the board with an adhesive material such as epoxy resin having a strong adhesive force. The material of the board is selected from among materials whose thermal expansion coefficients are the same as that of silicone (for example, a silicone board or crystallized glass).

In the case of the soft bonding, in order to relax thermal strain in the board or stress during assembly, a pressure sensor chip is bonded to a board by using a silicone-rubber type of adhesive silicone. Accordingly, the material of the board can be selected from a wide variety of materials such as metals, plastics and the like. In general, stress derived from the board adversely affects the output characteristics of the pressure sensor to deteriorate the performance of the sensor to a remarkable extent. However, the use of the soft bonding makes it possible to maintain the performance of the sensor at a high level. In order to utilize the soft bonding appropriately, as in the present invention, pressure is preferably applied to the upper surface of the pressure sensor chip so as to enable this sensor chip and the board to integrally support the pressure.

Unlike the present invention, if pressure is applied to the pressure sensor chip from the reverse side thereof, a peeling force may act on the soft adhesive, thus leading to a deterioration in the soft bonding force. If a pressure whose response is fast is applied, pressure relaxation will occur due to the soft adhesive. As a result, accurate pressure measurement may become impossible or the phenomenon of creep may be caused.

The pressure-transmitting medium 21 charged in the coupling lid 20 is made of a gel-like material having a high degree of electrical insulation effect and a low elastic coefficient, for example, a silicone gel. This gel having such an electrical insulation effect is utilized as an insulating and isolating sealant, and serves to transmit fluid pressure to the diaphragm of the sensor chip 18 without any transmission loss. In addition, since this gel is fully charged into the hollow space of the coupling lid 20, no bubble is generated in this hollow space.

Accordingly, the aforesaid pressure transducer 10 provides the following advantage (i).

(i) Since pressure fluctuations in the fluid chamber 15 are transmitted to the sensor chip 18 through the pressure-transmitting medium 21 made of a silicone gel, it is possible to prevent the fluid from coming in contact with the sensor chip 18, whereby the sensor chip 18 can stably sense the pressure fluctuations alone. In other words, the silicone gel consisting of stable material undertakes to transmit pressure from the fluid chamber 15 to the pressure sensor chip 18. Accordingly, no pressure loss appears above the sensor chip 18, whereby temperature stability and electrical safety are improved to enable an even higher-precision pressure measurement.

The sensor chip 18, which is surrounded on the insulating board 19 by the coupling lid 20, and the associated wiring are coated with a thin film of fluororesin.

Accordingly, the aforesaid pressure transducer 10 provides the following advantage (j).

(j) An organic coating employing fluororesin is applied to the entire sensor chip 18 and is isolated from corrosion and unwanted electrical conduction due to a fluid. Ordinarily, owing to the aforesaid silicone gel, the sensor chip 18 and the associated wiring are protected against corrosion and unwanted electrical conduction due to a fluid. In addition, electrical safety with respect to the organism is doubly ensured by the aforesaid coating. Even if the present apparatus is used for a long time, electrical safety with respect to patients is not impaired.

Figure 12:
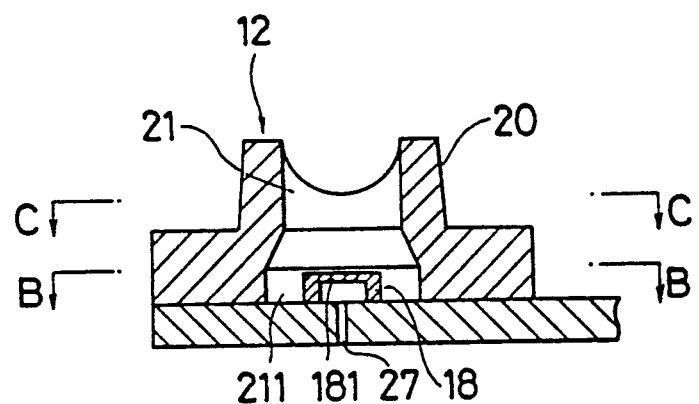
FIG. 12 is a cross-sectional view showing the sensor assembly.
Figure 12:
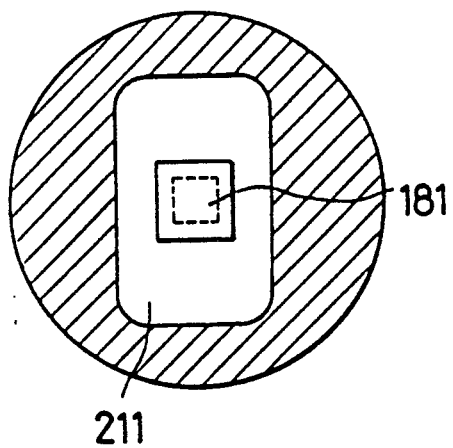
Figure 12:
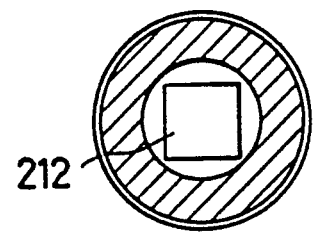
Figure 12:
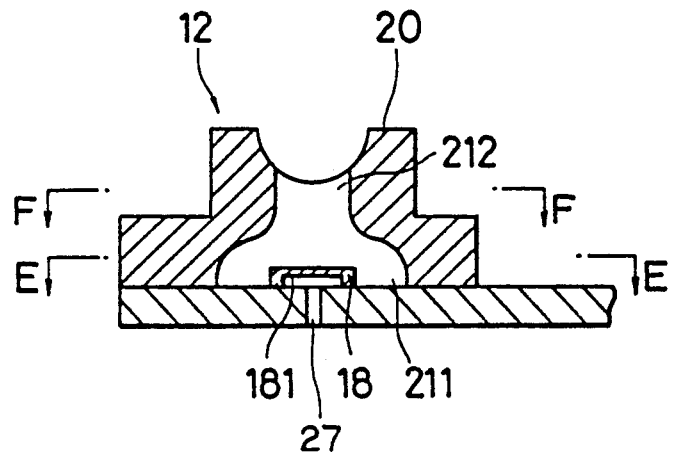
Figure 12:
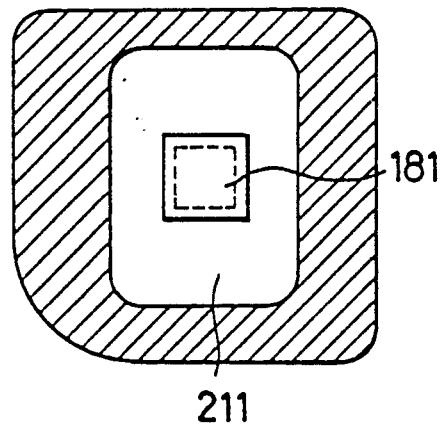
Figure 12:
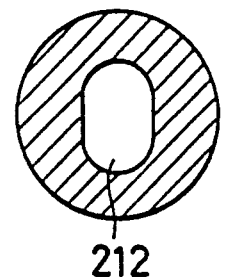

As shown in FIGS. 12(A) to 12(C), the coupling lid 20 of the sensor assembly 12 is made of polycarbonate resin, and has an overall height of 4.5 mm. The coupling lid 20 has a cylindrical base with a diameter of 10 mm and a height of 2 mm. The tapered portion has a lower-end diameter of 5.5 mm, an upper-end diameter of 5 mm, and a height of 2.5 m. As shown in a cross-sectional view taken along line B—B, a large inner space 211 which accommodates the sensor chip 18 has an approximately rectangular sectional configuration of 5×7 mm and a height of 1 mm. A samll inner space 212 which communicates with the fluid chamber 15 has a circular configuration with a diameter of 3 mm in cross section and a height of 3.5 mm. The pressure sensitive gauge portion of the sensor chip 18 is formed on a diaphragm portion 181 over a 1-mm$^2$ area thereof, and the small inner space 212 of the coupling lid 20 which communicates with the fluid chamber 15 has a cross-sectional area of 7.07 mm$^2$. Accordingly, the ratio of the former area to the latter area is selected to be approximately 7 times. The elastic modulus of the silicone gel which is used as the pressure-transmitting medium charged into the inner space of the coupling lid 20 is suitably $3\sim10\times10^3$ kg/mm$^2$.

As shown in FIGS. 12(D) to 12(F), the coupling lid 20 is, in another form, made of polycarbonate resin, and has an overall height of 4.5 mm. As is apparent from a cross-sectional view taken along line E—E, the base has a approximately square configuration in cross section with 9.5×9.5 mm and a height of 1.7 mm. The head portion of the coupling lid 20 is of a straight cylindrical configuration with a diameter of 5.5 mm and a height of 2.5 mm. As shown in a cross-sectional view taken along line E—E, the large inner space 211 which accommodates the sensor chip 18 has an approximately rectangular sectional configuration of 5×7 mm and a height of 1 mm. As shown in a cross-sectional view taken along line F—F, the small inner space 212 which communicates with the fluid chamber 15 has an elliptic configuration consisting of a combination of a rectangle of 1×2 mm and two semicircles each having a radius of 1 mm. The height of the small inner space 212 is 1.3 mm. The area of the diaphragm portion 181 of the sensor chip 18 is 1 mm$^2$ (1×1 mm), and the small inner space 212, which communicates with the aforesaid fluid chamber 15, has a cross-sectional area of 5.14 mm$^2$. Accordingly, the ratio of the former area to the latter area is selected to be approximately 5 times.

Accordingly, the aforesaid pressure transducer 10 provides the following advantage (k).

(k) It is possible to ignore pressure loss which results from shearing deformation which may occurs when the pressure-transmitting medium made of the silicone gel comes into the inner-diameter portion of the coupling lid 20. Accordingly, stable and high-precision pressure measurement can be realized.

If the aforesaid area ratio is 5 or less, shearing forces will act on the peripheral portion of the pressure-transmitting medium, so that the fluid pressure to be measured is absorbed. As a result, the accuracy of measurement may deteriorate.

Figure 10:
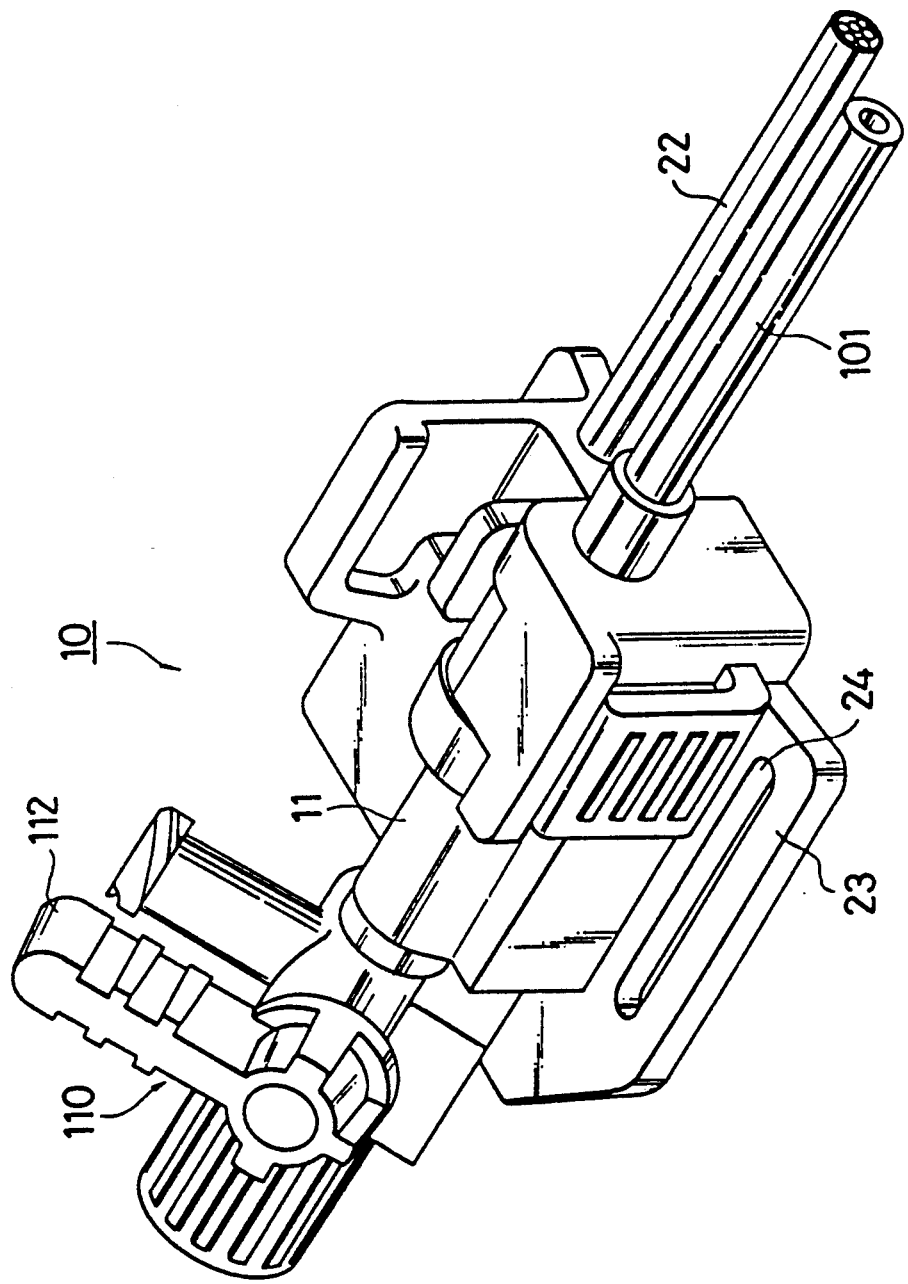
FIG. 10 is a perspective view showing an example in which the valve shaft of a three-way stop cock is arranged in an inclined manner in the pressure transducer apparatus.

The pressure transducer 10 is constructed such that, at the inlet portion of the fluid chamber 15, the housing 11 is integrally combined with a flushing device (flow control device) 100 which can be connected to an external sterilized-liquid supply source and which is capable of limiting the flow rate of the sterilized liquid. In addition, a three-way stop cock 110, which enables the flow passage of the liquid to be altered, is also integrally provided at the outlet portion of the fluid chamber 15. The flushing device 100 is connected to an introducing circuit 101 for introducing a flushing liquid such as an agent for preventing coagulation of the liquid, a saline solution or the like. The three-way stop cock 110 is connected to a blood circuit 111 or the like of the organism. If the three-way stop cock 110 is arranged such that its valve shaft is inclined as shown in FIG. 10, it is possible to improve the readiness of operation of a knob. The flushing device 100 includes a flushing holder 102, a body 103, a capillary bore 104, a flushing valve 105, a flushing knob 106, a flushing lever 107, a cock lever 112, and a Luer lock 113.

The flushing device 100 is constructed such that the flushing valve 105 made of silicone rubber overlies the ordinary body 103 made of polycarbonate resin. The flushing valve 105 servers to close the communication through-hole formed in the body 103 in a normal state. When the flushing valve 105 is displaced by means of the knob 106, it opens this communication through-hole. Moreover, in the normal state, the flushing device 100 continues transferring the sterilized fluid through the capillary bore 104 at a small rate in order to prevent the fluid from coagulating in the blood circuit. This small rate at which the fluid is continuously transferred is set to 1.5 ml/hr when the differential pressure between blood pressure and the pressure of flushback sustained in the flushing device 100 is 100 mmHg, and to 3.0 ml/hr when such differential pressure is 200 mmHg. When the flushing knob 106 is actuated to open the flushing valve 105, the sterilized fluid is supplied to the blood circuit at a rate of 10.0 ml/10 seconds.

The three-way stop cock 110 is constructed such that a valve 110V made of high-density polyethylene resin is rotatably included in a valve box 110H made of polycarbonate resin. The valve box 110H is provided with a first communication port 110A connected to the outlet portion of the fluid chamber 15 and a second communication port 110B connected to a path for transmitting the fluid pressure to be measured, the first and second communication ports 110A and 110B being arranged in alignment with each other. The valve box 110H is also provided with a third communication port 110C which is located in the direction perpendicular to a straight line which connects the first and second communication ports 110A and 110B and a fourth communication port 110D which opposes the third communication port 110C. The valve 110V is provided with three channels which perpendicularly intersect in a T-shaped configuration, so that at least three of the aforesaid communication ports 110A to 110D can communicate with one another.

The fluid chamber 15 of the housing 11, the flushing device 100 and the three-way stop cock 110 are arranged in alignment. A port, from which the electrical cable 22 extends, is disposed on the side of the housing 11 on which the flushing device 100 is disposed, the electrical cable 22 serving to connect the insulating board 19 to the external measuring device. The direction in which the electrical cable 22 is extended is the same as the direction in which the fluid passage 101 extends from the flushing device 100. With this arrangement, when the pressure transducer 10 is secured to an organism, the fluid circuit and the electrical cable 22 which extend from the flushing device 100 and the three-way stop cock 110 can be arranged along the upper arm of the organism. In addition, a web 23 is formed at the opposite ends of the area of the housing 11 which is connected to an external fluid circuit. Each of the webs 23 has a slit 24 and a curvature which enables the pressure transducer 10 to be removably secured to the upper arm of the organism by means of a belt easily and safely.

Accordingly, the aforesaid pressure transducer 10 provides the following advantage ①.

① The flushing device 100, which can be connected to an external sterilized-liquid supply source and which is capable of limiting the flow rate of the sterilized liquid, is formed integrally with the inlet portion of the fluid chamber 15 of the housing 11, and the three-way stop cock 110, which enables the flow passage of the liquid to be altered, is formed integrally with the outlet portion of the fluid chamber 15. Accordingly, since there is no need for the operation and connecting the flushing device 100 or the three-way stop cock 110, it is possible to lighten the burden imposed on medical workers. Moreover, it is possible to minimize the flow-passage length required to incorporate the flushing device 100 and the three-way stop cock 110, with the result that the dynamic response of pressure sensing is improved and the accuracy of pressure measurement can be therefore improved. In addition, since the flushing device 100 and the three-way stop cock 110 are formed integrally with the housing 11, it is possible to reduce the number of connections. As a result, since no bubble enters from connections or the like due to leakage, the dynamic response of pressure sensing is not lowered.

There is no risk of any connected pipe being coming off since the sensor assembly 12, the flushing device 100 and the three-way stop cock 110 are integrally combined. This means that, even if the fluid to be measured is, for example, artery blood having a high pressure of 120-150 mmHg, safe operation is realized since there is no risk that the blood spills due to accidental separation between the connections.

In the aforesaid pressure transducer 10, a pressure-waveform correcting device (air damping device) 120 is combined integrally with the aforesaid three-way stop cock 110. The pressure-waveform correcting device 120 is provided with an air chamber and a resistance portion which communicates with an opening formed in the three-way stop cock 110. The pressure-waveform correcting device 120 is arranged to damp anomalous pressure waves, which are transmitted to the sensor chip 18 through the three-way stop cock 110, by allowing the fluid in the three-way stop cock 110 to flow into the aforesaid air chamber through the resistance portion.

Figure 13:
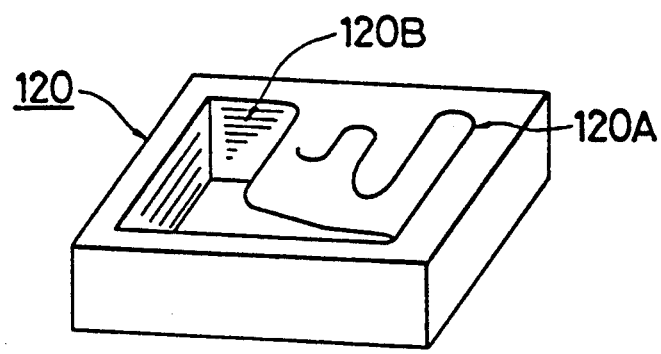
FIG. 13 is a diagrammatic view showing the pressure-waveform correcting device.
Figure 14:
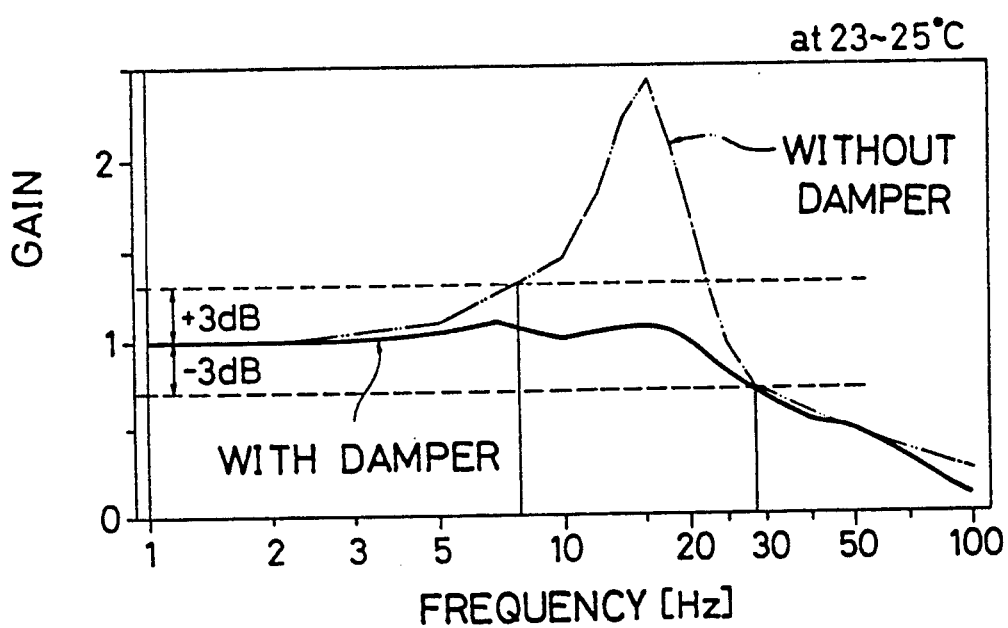
FIG. 14 is a graph showing the damping characteristics of the pressure-waveform correcting device.

As shown in FIG. 13, the pressure-waveform correcting device 120 is made from a plastic rectangular pallalepiped having a length of 12 mm, a width of 7 mm, and a height of 3.4 mm. The plastic rectangular pallalepiped is provided with a resistance portion 120A and a 60 $\mu$l air chamber 120B. The resistance portion 120A consists of a serpentine (sinuously winding) narrow flow passage having a length of 18 mm, a width of 0.2 mm, and a height of 0.27 mm, and the air chamber 120B is connected to the terminal end of the resistance portion 120A. The initial end of the resistance portion 120A is adapted to communicate with the third communication port 110C (with an inner diameter of 0.6 mm) of the three-way stop cock 110. The pressure of the organism, which is propagated through a blood flow passage including various kinds of sticking needles which are connected to the three-way stop valve 110, is combined with the pressure of the organism on the basis of the fluid resonance characteristics of that flow passage, thereby propagating an unnecessary resonance waveform to the fluid chamber. Thus, the sensor chip 18 makes measurement of blood pressure including the resonance waveform. The three-way stop cock 110 is connected to the pressure-waveform correcting device 120 in fluidic relationship so that a resonance waveform in the vicinity of, for example, 15 Hz which is propagated through the flow passage as shown in FIG. 14 is made flat by utilizing the resistance component of the resistance portion 120A and the capacity component of the air chamber 120B. In this manner, accurate measurement of pressure is enabled.

In the pressure-waveform correcting device 120, the resistance portion 120A is made serpentine in a plane. Accordingly, even in a small space, it is possible to assure a long resistance component, hence the desired pressure damping performance, whereby improved measurement performance can be achieved even with a small apparatus.

The narrow flow passage of the resistance portion 120A may be made from a straight line, a combination of different straight lines or a combination of straight and curved lines.

Accordingly, the aforesaid pressure transducer 10 provides the following advantages (m), (n), (o), (p), (q) and (r).

(m) It is essentially impossible to avoid the occurrence of resonance in a fluid circuit or the penetration of incidental bubbles. The pressure-waveform correcting device 120 is aimed at improving dynamic response during pressure measurement, and is used in combination with the sensor assembly 120. As the position of the pressure-waveform correcting device 120 which serves to eliminate resonance or the like is made closer to that of the sensor assembly 12, it is possible to render more remarkable the effect of eliminating the resonance occurring between the sensor assembly 12 and the pressure-waveform correcting device 120.

(n) By switching the three-way stop cock 110, the path for transmitting the fluid pressure to be measured can be selectively connected to or shut off from the sensor assembly 12, the third communication port 110C can be selectively connected to or shut off from the pressure-waveform correcting device 120 and the communication port 110D, or the fourth communication port 110D can be used for injection of remedy or sampling of blood. In addition, the pressure-waveform correcting device 120 can be selectively connected to or shut off from the fluid flow passage, thereby enabling the effect of waveform correction to be observed.

When the pressure-waveform correcting device 120 is in no use, the pressure-waveform correcting device 120 is shut off from the fluid from passage to prevent the air in the air chamber 120B from being discharged from the air chamber resulted from such as the vacuum created in the fluid flow passage by the erroneous operation of the syringe. Accordingly, it is possible to keep constant the air capacity in the air chamber so that the damping performance can be maintained in a proper state.

(o) By switching the three-way stop cock 110, the path for transmitting the fluid pressure to be measured can be selectively connected to or shut off from the sensor chip 18, or the third communication port 110C can be used for correction of pressure waveforms (damper), monitoring of pressure, injection of remedy, sampling of blood, or the like.

(p) By switching the three-way stop cock 110, the path for transmitting the fluid pressure to be measured can be selectively connected to or shut off from the sensor chip 18, or the third and fourth communication ports 110C and 11D can be used for correction of pressure waveforms (damper), monitoring of pressure, injection of remedy, sampling, or the like.

(q) In the aforesaid pressure transducer 10, a flushing liquid such as a saline solution or the like in a flash bag which is connected to the flushing device 100 which is integrally secured to the housing 11 is initially introduced into the fluid chamber 15 of the housing 11 by pressing the flusing lever 107, and is then introduced into a fluid circuit of an organism through the three-way stop cock 110 so that fluctuations in blood pressure are measured with the pressure transducer 10 connected to a catheter, which retains itself in the organism. In a conventional type of pressure transducer, since the flushing device 100 and the three-way stop cock 110 are prepared as separate devices, the operation of connecting them and charging them with a liquid is needed. Since the pressure transducer 10 according to the present invention is provided with the flushing device 100 and the three-way stop cock 110 in an integral form, the functions of these devices can be realized with a compact arrangement. Moreover, the overall flow passage is straight and short, whereby, even if a flushing liquid such as a saline solution or the like is introduced, bubbles do not easily occur. Since the housing 11 is made of transparent material, whether or not bubbles have entered the fluid chamber 15 can be easily observed from the outside of the housing 11, whereby it is possible to readily extract bubbles and high-precision measurement of pressure can be realized. Ordinarily, the dynamic response of the pressure transducer is limited primarily by the length of the extension tube of an indwelling catheter of an indwelling needle, the compliance in flow passage and bubbles in flow passage, rather than the performance of the transducer itself. In addition to the above-described advantage that bubbles do not easily occur, the flushing device 100 and the three-way stop cock 110 are integrated in the pressure transducer 10 of the present invention, whereby the overall length of the flow passage can be reduced to improve dynamic response. Moreover, the pressure transducer 10 can be secured to the organism safely as described previously, whereby neither discomfort nor pain is inflicted on a patient even when blood pressure is monitored for a long time. The direction in which the electrical cable 22 extends to the external measuring device is selected so as not to hinder the medical operation of a doctor, a nurse and the like. Accordingly, it is possible to realize stable pressure measurement.

(r) Since the resistance portion 120A of the pressure-waveform correcting device 120 is formed as a serpentine flow passage, it is possible to assure a relatively long fluid resistance component in an area of the same size, whereby the desired pressure damping performance can be obtained.

Since the pressure-waveform correcting device 120 is provided in the pressure-transmitting path which leads to the sensor chip 18, the dynamic response of pressure can be improved and even more accurate measurement of pressure can be realized.

In the pressure transducer 10, it is desirable that the distance between the sensor assembly 12 and the flushing device 100 be made equal to or less than 3% of the overall length of the path for transmitting the pressure of a fluid to be measured, which path starts at the sensor assembly 12, (the length measured from the sensor assembly 12 through the three-way stop cock 110 to the end of a catheter which was connected to a blood vessel of a patient). With this arrangement, it was found that the influence which is exerted over the measurement accuracy of the sensor assembly 12 by the resonance occurring between the sensor assembly 12 and the flushing device 100 could be ignored. In this manner, the measurement performance can be improved.

Accordingly, in the pressure transducer 10, the integral combination of the sensor assembly 12 and the flushing device 100 and that of the three-way stop cock 110 and the pressure-waveform correcting device 120 provide the following merits (A) and (B) in terms of the measurement performance.

(A) OPERATIONAL MERIT (1) Since the operation of connecting the flushing device 100, the three-way stop cock 110 and the pressure-waveform correcting device 120 to the sensor assembly 12 is omitted, the setup time is shortened.

② Since the flushing device 100, the three-way stop cock 110 and the pressure-waveform correcting device 120 are integrally bonded to one another in advance, there is no risk that the fluid spills due to an imperfect connection at each connection. In addition, it is possible to omit the operation of checking whether or not the connection at each part is perfect.

③ In a conventional type of arrangement in which the flushing device 100 and the sensor assembly 12 are connected by a tube, if the flushing devices 100 and the sensor assemblies 12 are arranged in two or three lines when in use for clinical operation, the sensor assemblies 12 are located separately from one another, with the result that the flushing device 100 in a line corresponding to a different assembly 12 may be mistakenly operated. In the pressure transducer 10, however, such a risk does not occur since the flushing device 100 is integrated with the sensor assembly 12. Moreover, it is possible to omit the operation of checking which measurement line a particular combination of the flushing device 100 and the sensor assembly 12 belongs to.

④ If a bubble should remain in the flow passage which extends from the flushing device 100 through the sensor assembly 12 and the three-way stop cock 110 to the pressure-waveform correcting device 120, the setting time can be reduced since the distance required to discharge the bubble from the flow passage through the three-way stop cock 110 or the like is short. When bubbles are to be discharged, it is customary to strike the sensor assembly 12. In this case, since the flow passage leading to the three-way stop cock 110 or the like is short, the probability that the bubble will be dispersed midway is reduced and it is therefore possible to reliably remove the bubbles.

⑤ It is not necessary for an operator to shift the visual axes to a great extent in order to check the presence or absence of remaining bubbles during priming or the like (it is possible to reduce the setting time). Incidentally, in the pressure transducer 10, since the housing 11, the flushing device 100 and the three-way stop cock 110 are made of transparent resin, the presence or absence of bubbles can be easily checked.

⑥ Even when the whole of the pressure transducer 10 is set to a bedside fixed panel, no complicated arrangement of the line is needed. Accordingly, it is possible to reduce the burden imposed on a nursing staff.

(B) MERIT IN TERMS OF MEASUREMENT PERFORMANCE

① As the pressure-waveform correcting device 120 is made closer to the sensor chip 18, the damping characteristics improves to a greater extent. In the pressure transducer 10, the distance between the sensor chip 18 and the pressure-waveform correcting device 120 is within, for example, about 15 mm, and the sensor chip 18 can be made closer to the pressure-waveform correcting device 120 compared to conventional types of pressure-waveform correcting devices. Accordingly, the measurement performance can be improved.

② In a conventional type of arrangement in which the flushing device 100, the three-way stop cock 110 and the pressure-waveform correcting device 120 are connected to the sensor assembly 12, a step may be formed or a flow passage may bend in the portion of each connection at which a female Luer-tapered inner surface and a corresponding male Luer-tapered end are engaged with each other. As a result, stagnant bubbles may remain in such portions and adversely affect the measurement performance. In contrast, in the pressure transducer 10, no step is formed in any flow passage and the flow passage is straight, whereby there is no possibility that stagnant bubbles remain.

③ Since the length of the flow passage which extends from the flushing device 100 through the sensor chip 18 and the three-way stop cock 110 to the pressure-waveform correcting device 120 is small, the probability that bubbles will enter is small.

④ Since there is no connections among the flushing device 100, the sensor assembly 12, the three-way stop cock 110 and the pressure-waveform correcting device 120, there is no risk that bacteria enter through each connection or they proliferate at each connection.

⑤ Since there is no tube or connector among the flushing device 100, the sensor assembly 12, the three-way stop cock 110 and the pressure-waveform correcting device 120, the dynamic pressure transmission characteristics are not influenced by the compliance of the material in itself of the tube or the connector.

⑥ In a case where bubbles remain in the measuring circuit of a conventional type, the influence of the compliance of the bubbles on the dynamic pressure transmission characteristics may result, an indwelling needle or an indwelling catheter may clog due to a thrombus, bending or the like, or the influence on the dynamic pressure transmission characteristics due to squeezing resistance resulting from the narrowness may result. In consequence, the measuring circuit may be overdamped (excessively damped). In contrast, in the pressure transducer 10, since the pressure-waveform correcting device 120 is integrated with the three-way stop cock 110, the pressure-waveform correcting device 120 can be turned off by switching the valve of the three-way stop cock 110, whereby the overdamped state can be readily cancelled.

Figure 8:
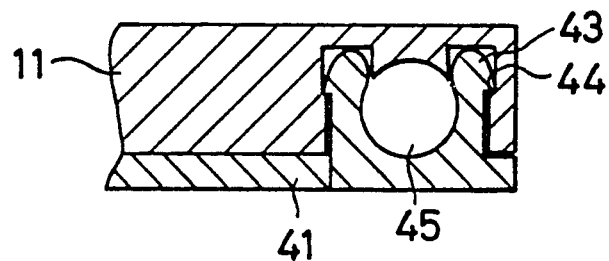
FIG. 8 is a cross-sectional view showing the bonding structure between a housing and a reverse lid.
Figure 9:
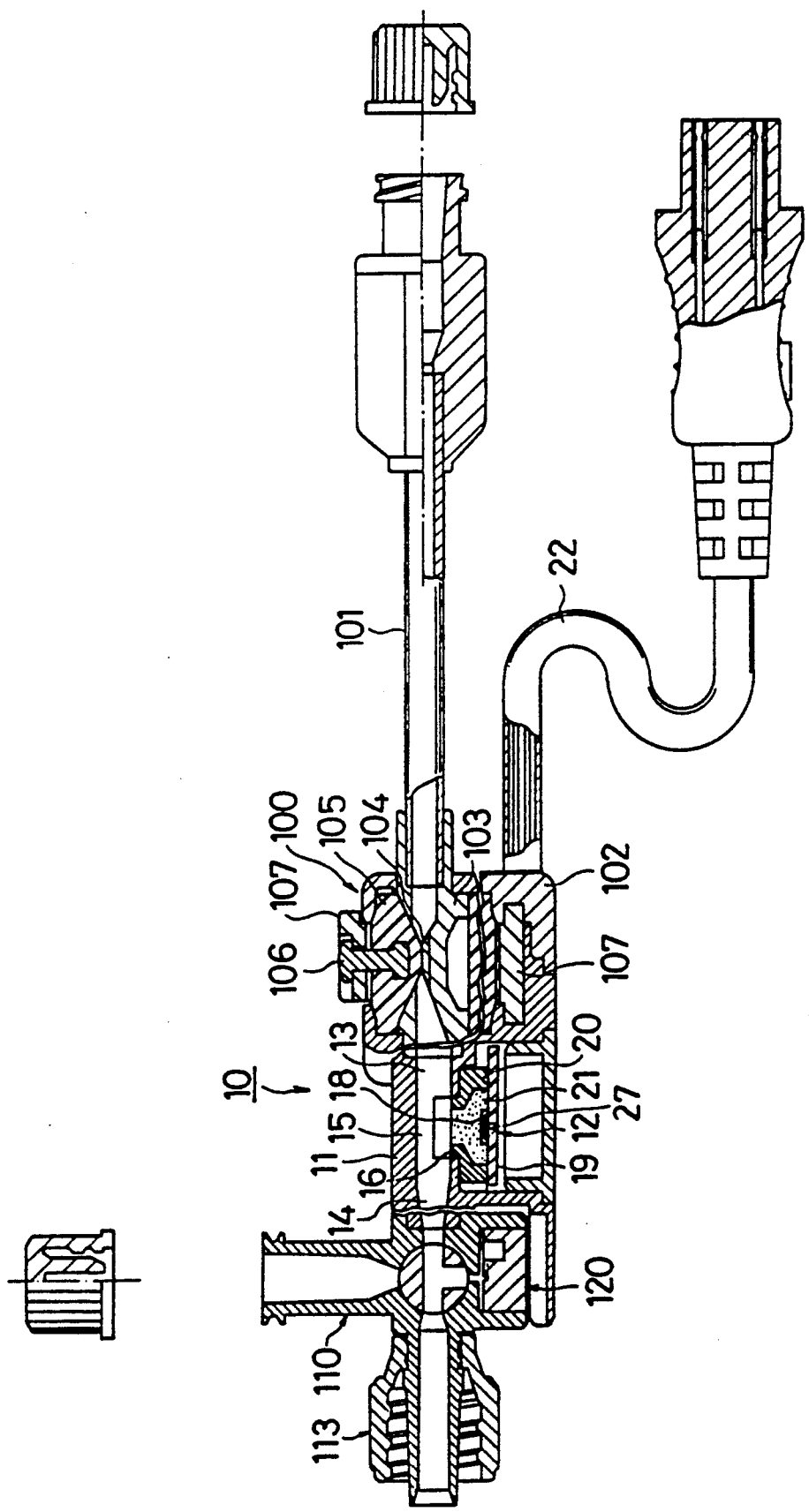
FIG. 9 is a cross-sectional view showing the overall structure of the disposable pressure transducer apparatus.

Accordingly, when the sensor assembly 12 which is constructed in the above-described manner is inserted and fixed in the housing 11, as described above, an adhesive such as epoxy resin is applied to both the stepped portion of the coupling lid 20 which is formed below its taper and the peripheral portion of the lower edge of the taper of the communication through-hole 16, and the connection between the coupling lid 20 and the communication through-hole 16 is made liquid-tight by adhesive sealing. Thereafter, the reverse side of the sensor-accommodating chamber 17 of the housing 11 is sealed with the reverse lid 42 having an edge 41 around its periphery by means of an adhesive or a plastic solvent so that the sensor assembly 12 is made liquid-tight. In this case, as shown in FIG. 8, an engagement portion 43 having elasticity may be partially formed on the reverse lid 42, and an engagement portion 44 which can engage with the engagement portion 43 may be formed on a corresponding portion of the housing 11. With this arrangement, it is possible to physically tightly engage the reverse lid 42 with the housing 11. Accordingly, when the reverse lid 42 is to be sealed by using an adhesive or a solvent, it is necessary to force the reverse lid 42 against the housing 11 until the adhesive becomes hard or the solvent transpires, and it is therefore possible to improve the productivity. The electrical cable 22 is inserted through the through-hole 45 shown in FIG. 8.

The sequence of assembly of each constituent part of the pressure transducer 10 is as follows.

① The body 103 of the flushing device 100 and the valve 105 are assembled together (refer to FIG. 11(A)).

② The flushing holder 102 and the flushing-liquid introducing circuit 101 are secured to the body 103 of the flushing device 100 and the valve 105 (refer to FIG. 11(B)).

③ The flushing device 100 of the above ② is secured to the housing 11 of the sensor assembly 12 (refer to FIG. 11(C)).

④ The pressure-waveform correcting device 120 together with a cover sheet 120C is secured to the valve box 110H of the three-way stop cock 110, and this three-way stop cock 110 is secured to the housing 12 of the sensor assembly 12 (refer to FIG. 11(D)).

In the aforesaid pressure transducer 10, the sensor assembly 12 constitutes the central portion of the pressure transducer 10 and, before the sensor assembly 12 which has been fabricated is incorporated into the housing 11, it is possible to evaluate the performance of the sensor assembly 12 which will be achieved when it is used as a pressure transducer. Accordingly, it is possible to easily make adjustment of sensitivity, offset and the like. In other words, since the performance of the desired pressure transducer can be finished in such an sub-assembled state, the yield of the pressure transducers 10 after assembly does not fall.

Moreover, the aforesaid pressure transducer 10 has the following advantages in that it has high performance but a low price. For example, the housing 11 is made from a plastic molding and can therefore be produced at a low cost. Since the central portion of the pressure transducer can be finished with the sensor assembly 12 alone, the efficiency of production is good and adjustment of the performance can be made in the sub-assembled state, whereby no defect occur during assembly. In addition, since the sensor chip 18 can be utilized in the form of a single element having no base board, the price can be made even more lower. Since the sensor assembly 12 utilizes only one surface of the insulating board 19, the efficiency of assembly and production is good. In assembly of the housing 11 and the sensor assembly 12, air-tightness can be realized by applying bonding to a single portion and the process is therefore simple.

The semiconductor pressure sensor chip used in the present invention is formed by forming a predetermined gauge portion on a wafer made of high-purity single-crystal silicon by photolithograph and introducing impurities which result from thermal dispersion or injection of ion into the gauge portion. The portion of the wafer, corresponding to the gauge portion, is removed to a thickness of over ten microns on its reverse side by chemical etching, thus forming a diaphragm. In addition, these gauge portion are connected by aluminum wiring or a diffusion lead so as to constitute a full bridge circuit. Accordingly, the gauge portions formed on the silicone diaphragm having a high degree of springiness are closely located in an area of several square millimeters, whereby all of them are placed in the same temperature environment.

As is apparent from principle of operation of the bridge circuit, when a pressure is applied, different pressures are applied to the gauge on adjacent sides so that an output proportional to the pressure is obtained. However, with respect to changes in environmental temperature, the resistances of the gauges vary in the same direction and no output voltage is provided. In the semiconductor pressure sensor chip developed by the present inventors, variations in the accuracy of gauge pattern and impurity-diffusion concentration are reduced to suppress variations in gauge which are integrally formed on a diaphragm, and temperature compensation is enabled only with the bridge-circuit arrangement. Accordingly, an additional resistor or a thermistor for compensating for temperatures is not needed, and the step of compensating for temperatures is omitted, whereby the price of the chip can be reduced.

The general method of using the apparatus of the present invention will be described below.

When the blood pressure of a patient is to be measured by means of the present apparatus, a blood communication circuit is connected to the three-way stop cock protion of the present sensor, the blood communication circuit having at one end a sticking needle which is stuck into and retained in a blood vessel of an organism. A sterilized-liquid supply source having pressure means is connected to a flushing device. In this manner, a rectilinear liquid communication circuit is formed between the sticking needle on the organism side and the sterilized-liquid supply source with the present sensor positioned in the center.

Then, the three-way stop cock is operated to place the organism and the sterilized-liquid supply source in communication with each other, that is to say, the first communication port is made to communicate with the second communication port. At this time, the fourth communication port is tightly closed. In the next operation, the lever of the flushing device is pressed to charge the sterilized liquid into the liquid communication circuit positioned between the sensor and the sticking needle. This operation is very important in order to realize accurate blood measurement. In other words, the operation needs to be executed very carefully, for if even small bubbles should enter the liquid communication circuit, the accuracy of blood measurement falls. The sterilized liquid charged in the liquid communication circuit is kept flowing from the tip of the sticking neeld. In this state, when the lever of the flushing device is released, the interior of the liquid communication circuit remains full of the sterilized liquid. In this state, the sticking needle is stuck into a predetermined blood vessel, and is retained and fixed with surgical tape or the like. At this time, it follows that the pressure of the organism is transmitted as pressure fluctuations in the blood vessel to the pressure sensor section through the sticking needle, the liquid communication circuit and the three-way stop cock. During the pressure measurement, the sterilized liquid, which contains an agent for preventing coagulation of the blood (such as heparin), is made to enter through a small hole in the flushing device, whereby the coagulation of the blood in the flow passage or in the sticking needle is prevented without hindering the pressure measurement. In such a pressure measurement, accurate pressure waveforms may not be obtained since a resonance waveform is combined with the pressure signal because of the size of the sticking needle or the length of the liquid communication circuit. For this reason, the lever of the three-way stop cock is operated to select the third communication port so that the pressure-waveform correcting device in communication with the third communication port can operate. In this manner, it is possible to eliminate the resonance waveform which is a primary cause of errors.

In accordance with the present invention, the following inventive features appear in the above-described process of measuring blood pressure, from the preparatory step to the completion of blood-pressure measurement.

Since all the portions between the sterilized-liquid supply source and the sticking needle are transparent, the presence or absence of bubbles can be determined.

Since the three-way stop cock, the pressure-waveform correcting device, the pressure sensor, and the flushing device are integrally constructed, the number of connections at which bubbles may penetrate is reduced.

Since the three-way stop cock, the pressure-waveform correcting device, the pressure sensor, and the flushing device are integrally constructed, the operations required to measure blood pressure are simple and all the process steps can be executed rapidly and safely.

Since the three-way stop cock, the pressure-waveform correcting device, the pressure sensor, and the flushing device are integrally constructed, the distance between these elements is short and the penetration of resonance waveforms, which may lead to errors in blood-pressure measurement, can be suppressed.

Since the pressure-waveform correcting device does not include many portions to be adjusted, it is possible to easily realize high-precision measurement of blood pressure.

The type of pressure transducer which constitues the disposable pressure transducer apparatus of the present invention is not limited to the type which utilizes the above-described sensor assembly 12. For example, the disposable pressure transducer apparatus may be constructed using a mechanical-electrical transducer of the type which comprises an elastic board made of signle-crystal silicone and fixed to a surface of a substrate along its peripheral portion, a strain-generating portion which is formed in the center of the elastic board and at which strain occurs due to external pressure, and a P-type senmiconductor strain-electricity converting device formed on a surface of the strain-generating portion. This transducer is arranged to pick up an electrical output proportional to the strain of the strain-generating portion with the strain-electricity converting device connected to a constant current source. In such a transducer, the average conductivity of the aforesaid strain-electricity converting device is $3.7 \times 10^2 \sim 6.0 \times 10^2 (1/\Omega cm)$, the aforesaid base substrate being made of an insulating material which has a coefficient of thermal expansion of $2.6 \times 10^{-} \sim 3.4 \times 10^{-6} (1/° C.)$, and the following relationship being $60 \sim 150$:

$$\frac{\text{the length of the short axis of the surface of the strain-generating portion}}{\text{(the thickness of the strain-generating portion)}}$$

As described above, in accordance with the present invention, it is possible to provide a disposable pressure transducer in which, although a sensor assembly in itself constitutes the central portion for pressure conversion, the number of constituent parts of the sensor assembly is small and the assembly process, hence the assembly operation, is simple, in which the construction of the sensor assembly is simple and pressure transmission characteristics are improved, and which can be safely handled and is excellent in measurement performance.

In accordance with the present invention, a disposable pressure transducer apparatus of the type which is used with its pressure transducer connected to an external sterilized-liquid supply source or with its three-way stop cock for altering the flow passage of a liquid connected to the outlet side of a housing, which apparatus makes it possible to improve the accuracy of pressure measurement and to reduce the burden imposed on medical workers and which is safe and excellent measurement performance.

What is claimed is:

1. A disposable pressure transducer apparatus comprising:
    a pressure transducer having a flow passage for a liquid and means for converting fluid pressure into an electrical signal;
    a pressure-waveform correcting device including means for, when said device is in communication with said flow passage, damping an anomalous pressure wave which is transmitted to said pressure transducer;
    a three-way stop cock comprising a valve box, and a valve rotatably disposed in said valve box;
    said valve box having:
        a first port in communication with said flow passage;
        a second port connected to a path for transmitting the fluid pressuref to be measured, said first and second ports being located in alignment with each other; and
        a third port located out of alignment with said first and second ports, said third port being in fluid communication with said pressure-waveform correcting device;
        said valve having three channels which intersect such that said first, second and third ports are placed by said channels in communication with one another only when said valve is at a given position;
        said pressure transducer, said pressure-waveform correcting device and said three-way stop cock being integrally combined into a single unit.

2. A disposable pressure transducer apparatus according to claim 1, wherein said damping means of the pressure-waveform correcting device comprises a resistance portion which is communicatable with said liquid in the flow passage by said valve, and an air chamber in communication with said resistance portion, which said resistance portion and air chamber are arranged to damp said anomalous pressure wave which is transmitted to said pressure transducer when said liquid in said flow passage flows into said air chamber through said resistance portion.

3. A disposable pressure transducer apparatus according to claim 2, wherein said resistance portion of said pressure-waveform correcting device is shaped from the group consisting of a straight line, a curve, a combination of straight and curved lines, and a combination of different straight lines, said air chamber being connected to a terminal end of the resistance portion.

4. A disposable pressure transducer apparatus according to claim 1, further comprising means for controlling flow rate of said liquid from a sterilized-liquid supply source to said flow passage of the pressure transducer.

5. A disposable pressure transducer apparatus according to claim 4, wherein said valve box further comprises a fourth port in alignment with said third port, the alignment between said first and second ports being perpendicular to the alignment between said third and fourth ports, and wherein said three channels of the valve intersect in a T-like configuration.

6. A disposable pressure transducer apparatus according to claim 1, wherein said valve box further comprises a fourth port in alignment with said third port, the alignment between said first and second ports being perpendicular to the alignment between said third and fourth ports, and wherein said three channels of the valve intersect in a T-like configuration.

7. A disposable pressure transducer apparatus according to claim 6, wherein said damping means of the pressure-waveform correcting device comprises a resistance portion which is communicatable with said liquid in the flow passage by said valve, and an air chamber in communication with said resistance portion, which said resistance portion and air chamber are arranged to damp said anomalous pressure wave which is transmitted to said pressure transducer when said liquid in said flow passage flows into said air chamber through said resistance portion.

8. A disposable pressure transducer apparatus according to claim 6, wherein said three-way stop cock places at least three of said first to fourth ports in communication with one another at predetermined positions of said valve other than said given position.

9. A disposable pressure transducer apparatus according to claim 1, wherein said third port is located perpendicularly to the alignment between said first and second ports, and wherein said three channels of the valve intersect in a T-like configuration.

10. A disposable pressure transducer apparatus according to claim 1, wherein said three channels of the valve place at least two of said three ports in communication with each other at positions of said valve other than said given position.

* * * * *

UNITED STATES PATENT AND TRADEMARK OFFICE
CERTIFICATE OF CORRECTION

PATENT NO. : 5,105,820
DATED : April 21, 1992
INVENTOR(S) : MORIUCHI et al.

It is certified that error appears in the above-indentified patent and that said Letters Patent is hereby corrected as shown below:

Title page:

Item [75], Inventors, line 2, "Inacaki" should be --Inagaki--
                         line 3, "Atsusi" should be --Atsushi--

Item [73], Assignee, delete "Tokyo, Japan", and insert:

--Tokyo; Kabushiki Kaisha Toyota Chuo Kenkyusho, Aichi; and Kabushiki Kaisha Tokai Rika Denki Seisakusho, Tokyo, all of Japan--.

Item [56] References Cited, Under "U.S. PATENT DOCUMENTS"

| Insert: | 4,444,198 | 4/1984 | Petre | 128/673 |
|---|---|---|---|---|
| | 4,576,181 | 3/1986 | Wallace et al | 128/675 |
| | 4,610,256 | 9/1986 | Wallace | 128/675 |
| | 4,644,797 | 2/1987 | Ichikawa et al | 73/706 |
| | 4,658,829 | 4/1987 | Wallace | 128/672 |
| | 4,679,567 | 7/1987 | Hanlon et al | 128/675 |
| | 4,686,764 | 8/1987 | Adams et al | 73/706 |
| | 4,779,625 | 10/1988 | Cole | 128/673--. |

UNITED STATES PATENT AND TRADEMARK OFFICE
CERTIFICATE OF CORRECTION

PATENT NO. : 5,105,820
DATED : April 21, 1992
INVENTOR(S) : Moriuchi, et. al.

It is certified that error appears in the above-indentified patent and that said Letters Patent is hereby corrected as shown below:

Under "FOREIGN PATENT DOCUMENTS"

Insert: -- 62-197730  9/1987  Japan --.

Item [62] after "Ser. No. 409,015, delete "Sep. 18, 1989.";

and insert: --(now U.S. Pat. No. 5,097,841).--

Signed and Sealed this

Twenty-sixth Day of August, 1997

Attest:

BRUCE LEHMAN

Attesting Officer

Commissioner of Patents and Trademarks